(12) United States Patent
Barker et al.

(10) Patent No.: US 7,470,258 B2
(45) Date of Patent: Dec. 30, 2008

(54) PRE-FILLED SAFETY VIAL INJECTOR

(75) Inventors: John M Barker, Ventura, CA (US);
Thor R. Halseth, Agoura, CA (US);
Joseph Kovalski, Ventura, CA (US);
Robert T. McWethy, Ventura, CA (US);
Bernardo Challiol, Ventura, CA (US)

(73) Assignee: MDC Investment Holdings, Inc.,
Wilmington, DE (US)

( * ) Notice: Subject to any disclaimer, the term of this patent is extended or adjusted under 35 U.S.C. 154(b) by 695 days.

(21) Appl. No.: 10/099,864

(22) Filed: Mar. 13, 2002

(65) Prior Publication Data

US 2002/0177819 A1 Nov. 28, 2002

Related U.S. Application Data

(60) Provisional application No. 60/275,569, filed on Mar. 13, 2001, provisional application No. 60/309,867, filed on Aug. 3, 2001.

(51) Int. Cl.
*A61M 5/32* (2006.01)
(52) U.S. Cl. ..................................... 604/192
(58) Field of Classification Search ................ 604/110, 604/181, 187, 195, 200–201, 203–206, 218, 604/220, 231–238, 244, 82–92, 191, 192, 604/197, 198, 199, 207, 213, 407, 411–415, 604/131, 134–136, 138, 139, 146, 228, 263, 604/137, 93.01, 141, 142, 143, 144, 147, 604/149, 140, 70, 81
See application file for complete search history.

(56) References Cited

U.S. PATENT DOCUMENTS

| | | | |
|---|---|---|---|
| 3,603,312 A | 9/1971 | Lucas et al. | |
| 3,826,261 A | 7/1974 | Killinger | |
| 3,882,863 A | 5/1975 | Sarnoff et al. | |
| 3,895,633 A | 7/1975 | Bartner et al. | |
| 4,051,852 A | 10/1977 | Villari | |
| 4,405,317 A | 9/1983 | Case | |
| 4,447,225 A | 5/1984 | Taff et al. | |
| 4,568,346 A | 2/1986 | van Dijk | |
| 4,592,742 A | 6/1986 | Landau | |
| 4,755,169 A | 7/1988 | Sarnoff et al. | |
| 4,861,335 A * | 8/1989 | Reynolds | ............ 604/88 |
| 4,904,243 A | 2/1990 | Bruera | |
| 4,972,843 A * | 11/1990 | Broden | ............ 600/573 |

(Continued)

*Primary Examiner*—Nicholas D Lucchesi
*Assistant Examiner*—Christopher D Koharski
(74) *Attorney, Agent, or Firm*—Stoel Rives LLP

(57) ABSTRACT

A method and apparatus for injecting medicine from a pre-filled container into a patient through an injection needle. After use, the needle is automatically shielded to prevent inadvertent contact with the needle. The device operates by pumping medicine out of the vial and into a transfer chamber. The medicine is then expelled from the transfer chamber into a patient during an injection stroke. At the end of the injection stroke, the needle is released for retraction, and the spring retracts the needle for shielding. The device can include an injector assembly and a vial holder assembly. The injector assembly has a needle retainer for releasably retaining the needle in a projecting position against the bias of a spring. The vial holder assembly is attachable with the injector assembly and is operable to transfer fluid from the vial and into the transfer chamber for an injection.

51 Claims, 11 Drawing Sheets

U.S. PATENT DOCUMENTS

| | | | |
|---|---|---|---|
| 4,994,029 A | 2/1991 | Rohrbough | |
| 5,067,948 A | 11/1991 | Haber et al. | |
| 5,114,033 A | 5/1992 | Golias et al. | |
| 5,167,641 A | 12/1992 | Schmitz | |
| 5,181,909 A * | 1/1993 | McFarlane | 604/506 |
| 5,199,949 A * | 4/1993 | Haber et al. | 604/88 |
| 5,279,796 A | 1/1994 | Parker et al. | |
| 5,292,318 A | 3/1994 | Haber et al. | |
| 5,330,426 A * | 7/1994 | Kriesel et al. | 604/89 |
| 5,354,284 A | 10/1994 | Haber et al. | |
| 5,358,489 A | 10/1994 | Wyrick | |
| 5,368,568 A | 11/1994 | Pitts et al. | |
| 5,393,497 A | 2/1995 | Haber et al. | |
| 5,400,923 A | 3/1995 | Golias et al. | |
| 5,468,233 A | 11/1995 | Schraga | |
| 5,487,738 A | 1/1996 | Sciulli | |
| 5,520,659 A | 5/1996 | Hedges | |
| 5,554,128 A | 9/1996 | Hedges | |
| 5,637,087 A * | 6/1997 | O'Neil et al. | 604/82 |
| 5,743,886 A | 4/1998 | Lynn et al. | |
| 5,795,336 A * | 8/1998 | Romano et al. | 604/192 |
| 5,873,859 A | 2/1999 | Muntz | |
| 5,989,237 A | 11/1999 | Fowles et al. | |
| 6,019,750 A | 2/2000 | Fowles et al. | |
| 6,022,339 A | 2/2000 | Fowles et al. | |
| 6,039,713 A * | 3/2000 | Botich et al. | 604/110 |
| 6,063,068 A | 5/2000 | Fowles et al. | |
| 6,071,270 A | 6/2000 | Fowles et al. | |
| 6,090,091 A | 7/2000 | Fowles et al. | |
| 6,090,092 A | 7/2000 | Fowles et al. | |
| 6,090,093 A | 7/2000 | Thibault et al. | |
| 6,099,510 A | 8/2000 | Ruther et al. | |
| 6,113,583 A | 9/2000 | Fowles et al. | |
| 6,159,192 A | 12/2000 | Fowles et al. | |
| 6,224,568 B1 | 5/2001 | Morimoto et al. | |
| 6,364,865 B1 * | 4/2002 | Lavi et al. | 604/411 |
| 6,607,508 B2 * | 8/2003 | Knauer | 604/131 |
| 2004/0111063 A1 * | 6/2004 | Botich et al. | 604/195 |

* cited by examiner

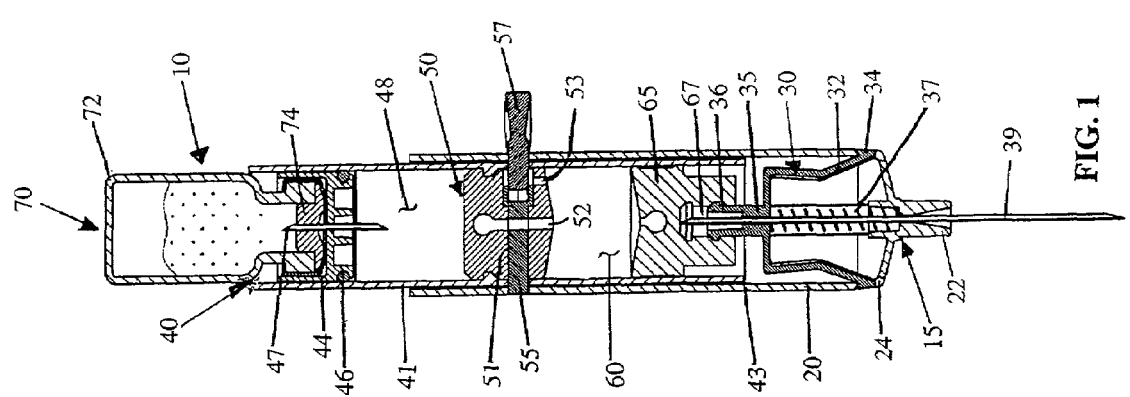
FIG. 1
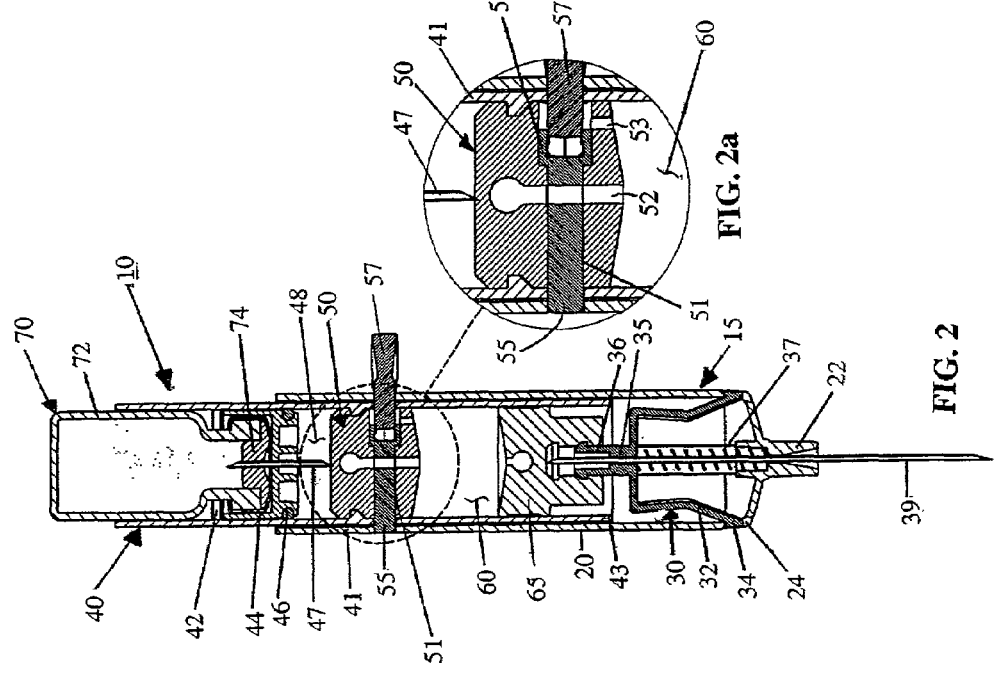
FIG. 2a
FIG. 2
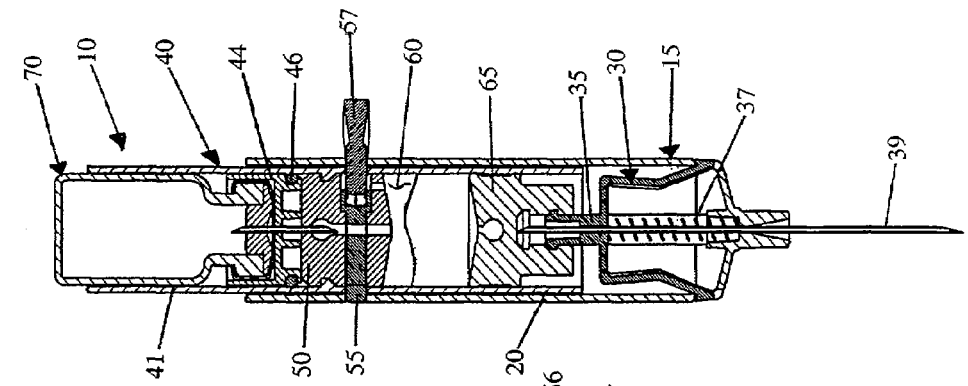
FIG. 3

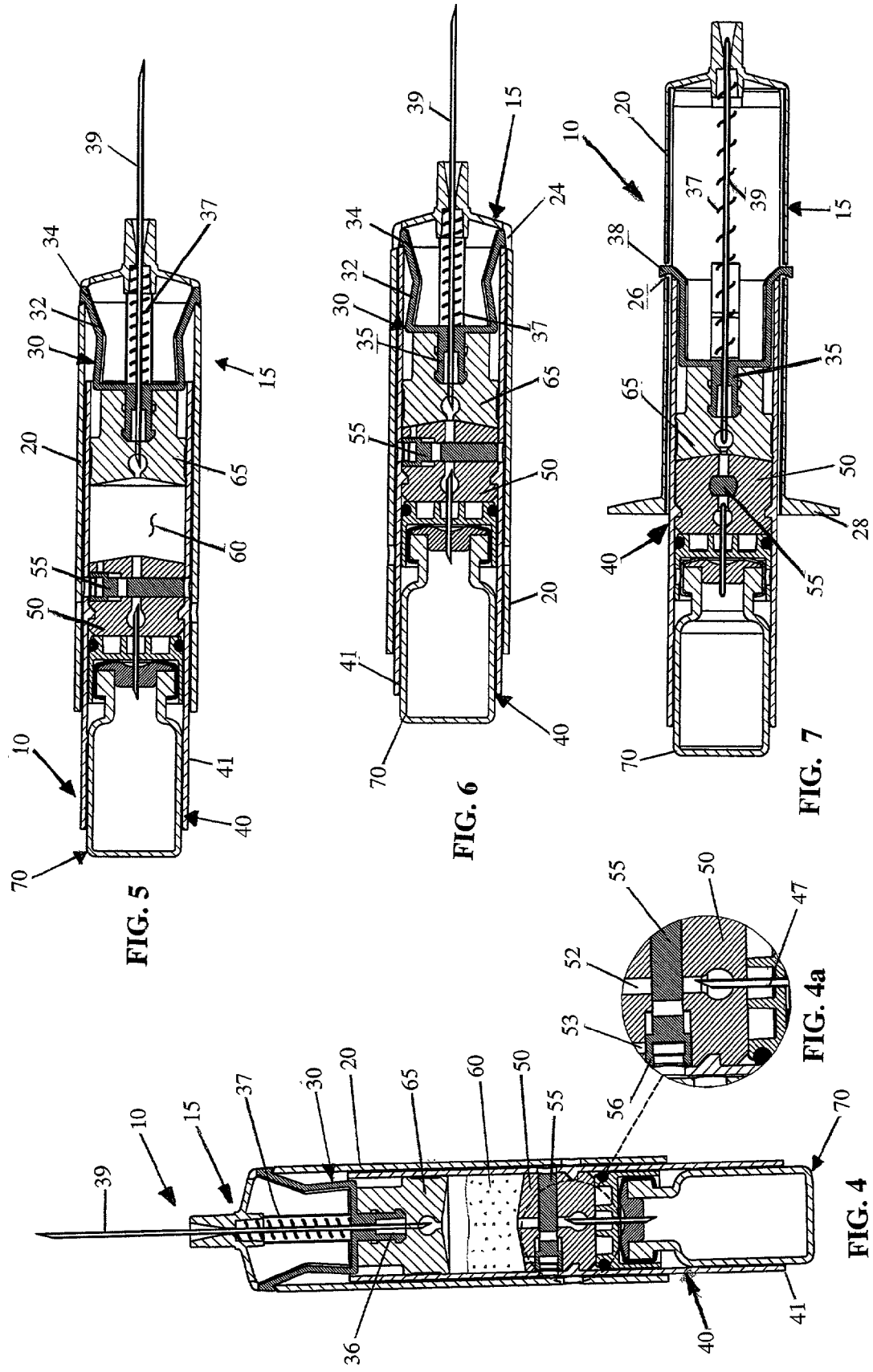

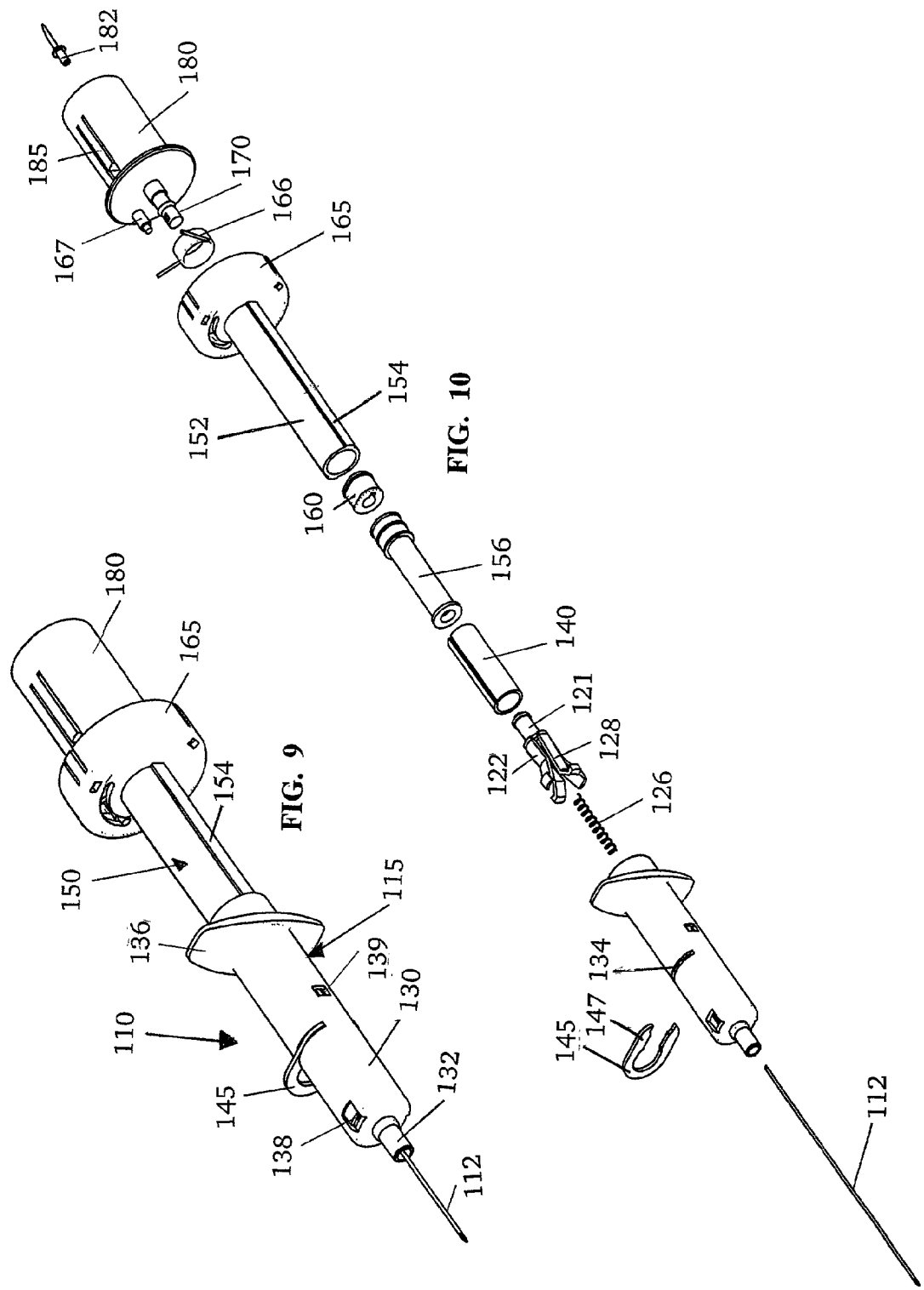

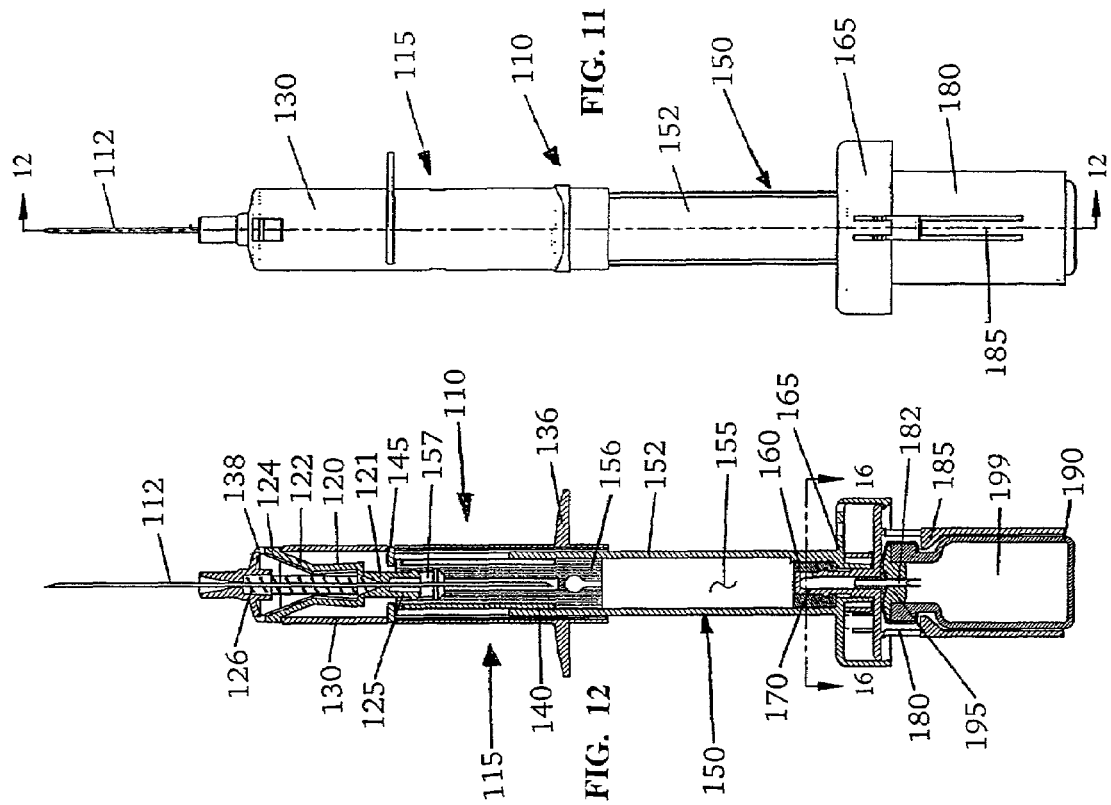

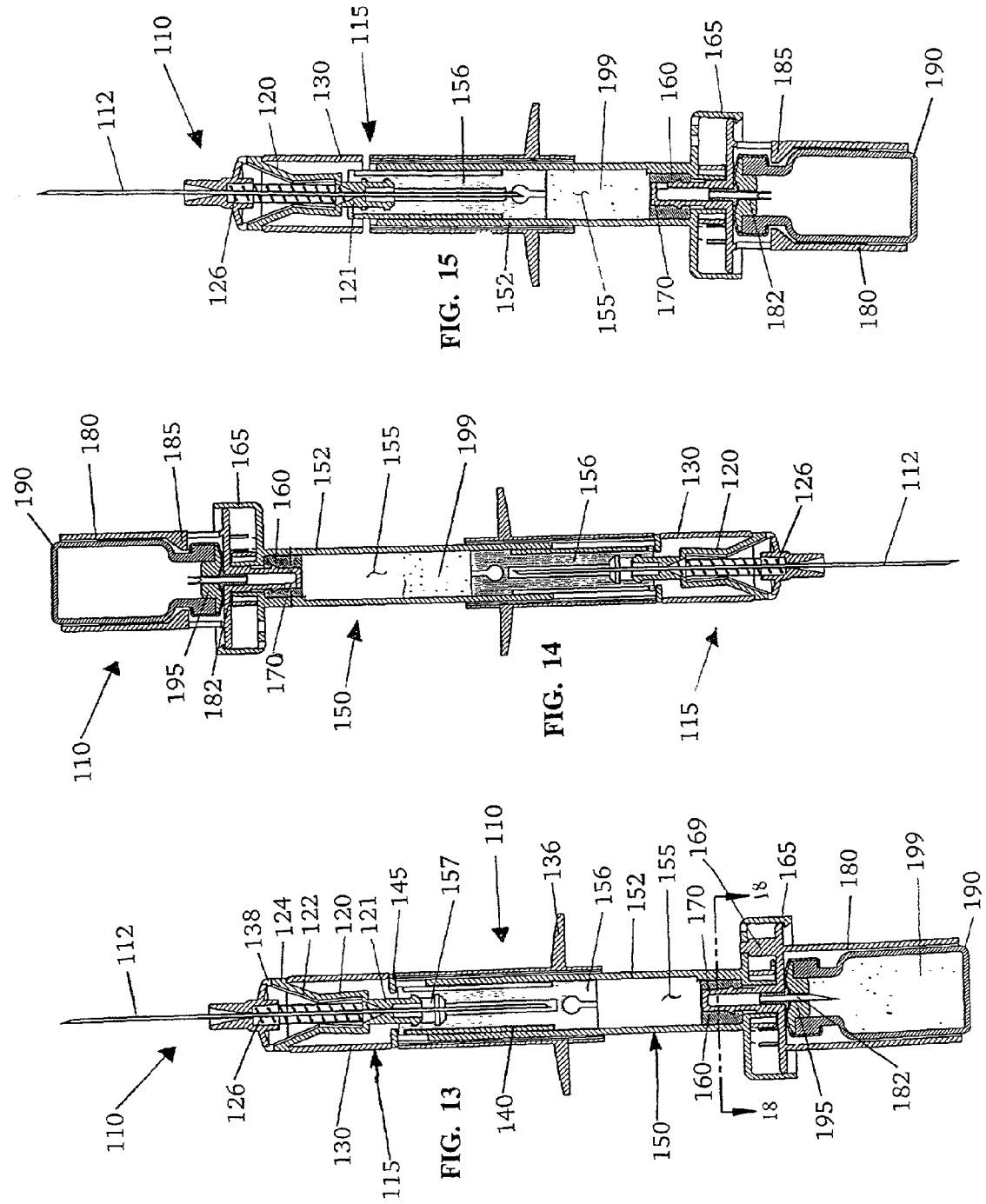

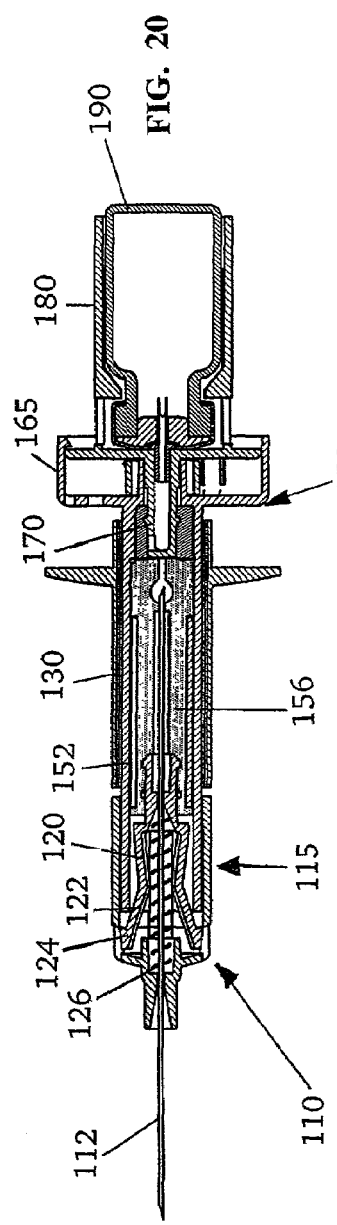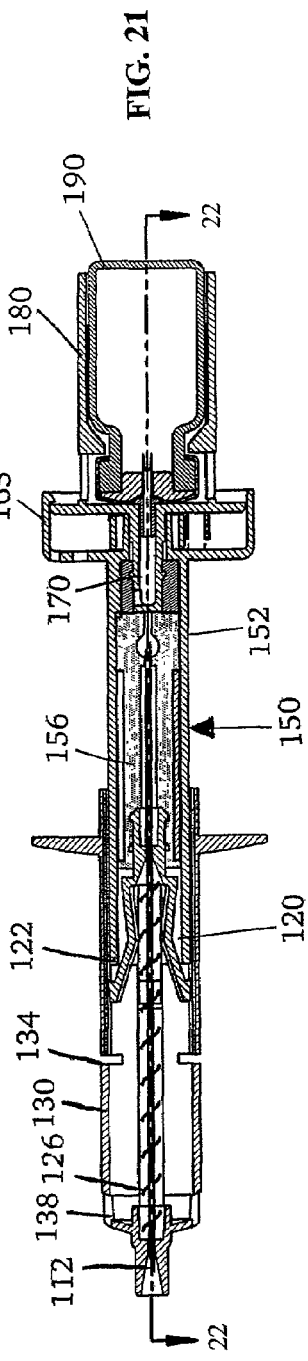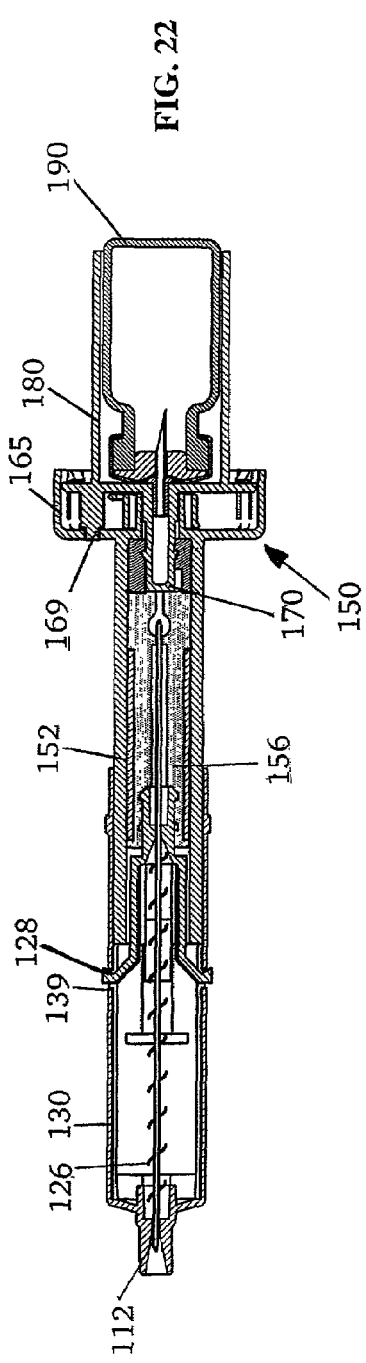

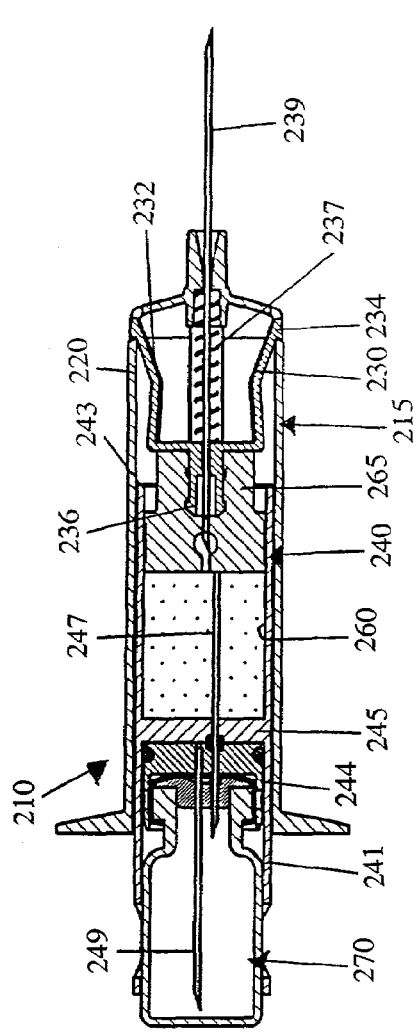
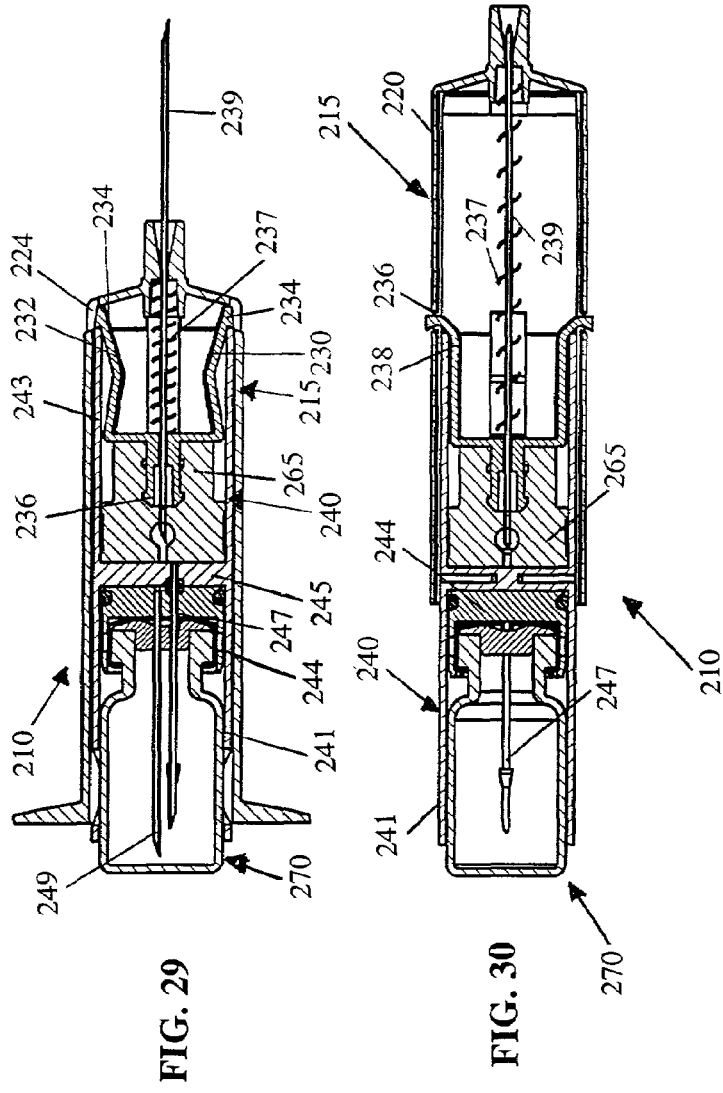
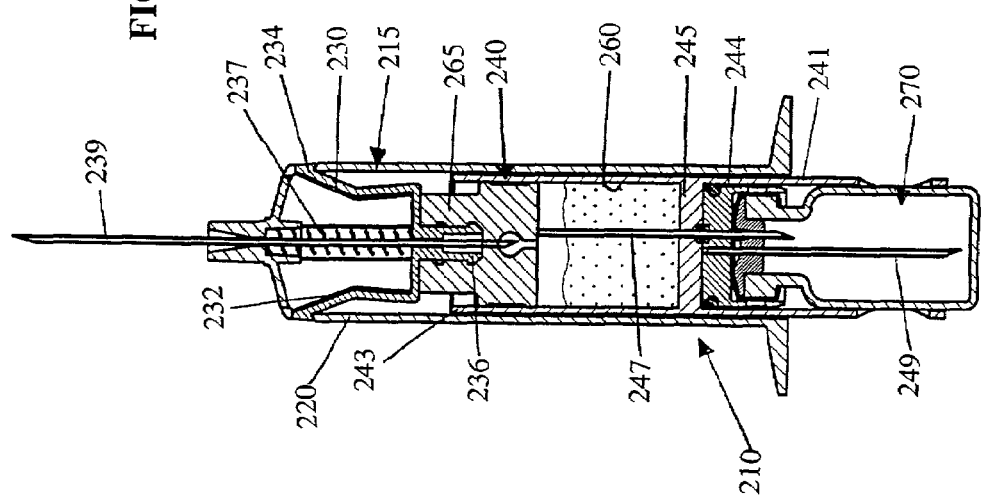
FIG. 27
FIG. 28
FIG. 29
FIG. 30

PRE-FILLED SAFETY VIAL INJECTOR

PRIORITY APPLICATIONS

The present application claims priority to U.S. Provisional Application No. 60/275,569 filed Mar. 13, 2001, and U.S. Provisional Application No. 60/309,867, filed Aug. 3, 2001. Each of the foregoing applications is hereby incorporated herein by reference.

FIELD OF THE INVENTION

The present invention relates to medical devices and more particularly to medical devices for injecting fluid from a pre-filled vial. After use, the needle is shielded to prevent inadvertent contact with the contaminated needle.

BACKGROUND

A common method for injecting medicine into a patient utilizes a vial of medicine and a standard syringe having a needle. The vial has a septum, which seals an end of the vial. To prepare for an injection, the medical professional draws back the plunger in the syringe so that there is a quantity of air in the syringe. The medical professional then pierces the vial septum with the needle and injects the air from the syringe into the vial to pressurize the medicine in the vial. The medicine is then drawn into the syringe from the vial by drawing back the plunger until the desired dose is in the syringe. The syringe is then removed from the vial's septum.

After the syringe is removed from the vial, the needle may be removed and replaced with a new needle either because the needle may become dulled by the vial septum or it may be desirable to utilize a smaller gauge needle for the injection. After the needle is replaced, air is purged from the syringe by inverting the syringe so that the needle faces upwardly, and the plunger is advanced to purge the air. The injection is then given to the patient.

Handling of such medical devices after the needle is withdrawn from the patient can result in transmission of various pathogens, most notably human immune virus (HIV), due to an inadvertent needle stick to medical personnel. Accordingly, it is desirable to create an easier, safer and more efficient manner for extracting medicine from a standard vial and injecting it into a patient.

SUMMARY OF THE INVENTION

In light of the shortcomings of the prior art, the present invention provides a method and apparatus for safely and easily injecting medicinal fluid from a pre-filled container.

One aspect of the present invention provides a device for injecting medicinal fluid from a vial, wherein the device has a transfer chamber for receiving fluid from the vial. The fluid is injected into a patient through a needle. After use, the needle is shielded to prevent contact with the contaminated needle. Preferably, but not necessarily, the needle is automatically retracted after use to shield the contaminated needle.

Another aspect of the present invention provides a device cooperable with a vial having fixed forward and rearward walls. A holder is configured to receive the vial, and a needle is provided for injecting medicinal fluid from the vial. A fluid path between the vial and the needle allows the medicinal fluid to flow from the vial to the injection needle. After use, the needle is protected to shield the contaminated needle against inadvertent contact. Preferably, the invention also provides a biasing element for retracting the needle and a needle retainer for releasably retaining the needle against the bias of the biasing element during use.

The present invention also provides a method for injecting medicine. The method comprises providing a container having a quantity of medicinal fluid and an injection device having a chamber and a needle. The container is attached to the device and the medicinal fluid is transferred from the container to the chamber. The medicinal fluid is then expelled from the chamber and the needle is retracted to shield the needle against inadvertent contact.

A further aspect of the present invention provides a method for injecting medicinal fluid from a container having first and second ends, in which the first and second ends are fixed to prevent displacement of the first end relative to the second end. An injection device having a needle is provided and the container is attached to the device. The medicinal fluid is expelled from the container through the needle and the needle is retracted to shield the needle against inadvertent contact.

Yet another aspect of the present invention provides a medical device cooperable with a needle assembly having a retractable needle and a pre-filled container of medicinal fluid. The device includes a housing cooperable with the needle assembly, a socket cooperable with the container and a pressurizing element operable to provide positive fluid pressure to the container when the container is disposed in the socket. A chamber in the housing is provided for receiving the medicinal fluid. The housing has an actuation surface cooperable with the needle assembly to shield the needle after use.

DESCRIPTION OF THE DRAWINGS

The foregoing summary as well as the following detailed description of the preferred embodiments will be best understood when read in conjunction with the following drawings, in which:

FIG. 1 is a cross-sectional view of a safety pre-filled vial injection device illustrating the device in a position prior to transfer of medicine from the vial;

FIG. 2 is a cross sectional view of the device illustrated in FIG. 1 illustrating the device after a pressurization stroke;

FIG. 2a is an enlarged detail of a portion of the device in FIG. 2, illustrating details of a control valve in the open position;

FIG. 3 is a cross-sectional view of the device illustrated in FIG. 1, illustrating the device after transfer of medicine from the vial;

FIG. 4 is a cross-sectional view of a portion of the device illustrated in FIG. 1, illustrating the device after the control valve is closed;

FIG. 4a is an enlarged detail view of a portion of the device in FIG. 4, illustrating details of the control valve in a closed position;

FIG. 5 is a cross-sectional view of the device illustrated in FIG. 1, illustrating the device in a ready to inject position;

FIG. 6 is a cross-sectional view of the device illustrated in FIG. 1, illustrating the device at the end of an injection stroke;

FIG. 7 is a cross-sectional view of the device illustrated in FIG. 1, illustrating the device after retraction;

FIG. 9 is a perspective view of an alternative embodiment of a safety prefilled vial injection device;

FIG. 10 is an exploded perspective view of the device illustrated in FIG. 9;

FIG. 11 is a side elevational view of the device illustrated in FIG. 9;

FIG. 12 is a cross-sectional view of the device illustrated in FIG. 11, taken along the line 12-12;

FIG. 13 is a cross-sectional view of the device illustrated in FIG. 12, illustrating the device after the vial has been pressurized;

FIG. 14 is a cross-sectional view of the device illustrated in FIG. 12, illustrating the device after fluid has been withdrawn from the vial;

FIG. 15 is a cross-sectional view of the device illustrated in FIG. 14, illustrating the device just prior to injection;

FIG. 20 is a cross-sectional view of the device illustrated in FIG. 15, illustrating the device after completion of an injection;

FIG. 21 is a cross-sectional view of the device illustrated in FIG. 20, illustrating the device after retraction of the needle;

FIG. 22 is a cross-sectional view of the device illustrated in FIG. 21, taken along the line 22-22;

FIG. 27 is a cross-sectional view of the device illustrated in FIG. 23, illustrating the device prior to venting the vial assembly;

FIG. 28 is a cross-sectional view of the device illustrated in FIG. 27, illustrating the device prior to injection;

FIG. 29 is a cross-sectional view of the device illustrated in FIG. 28, illustrating the device after injection; and FIG. 30 is a cross-sectional view of the device illustrated in FIG. 29, illustrating the device after retraction of the needle.

DETAILED DESCRIPTION OF THE PREFERRED EMBODIMENTS

Figure 8:
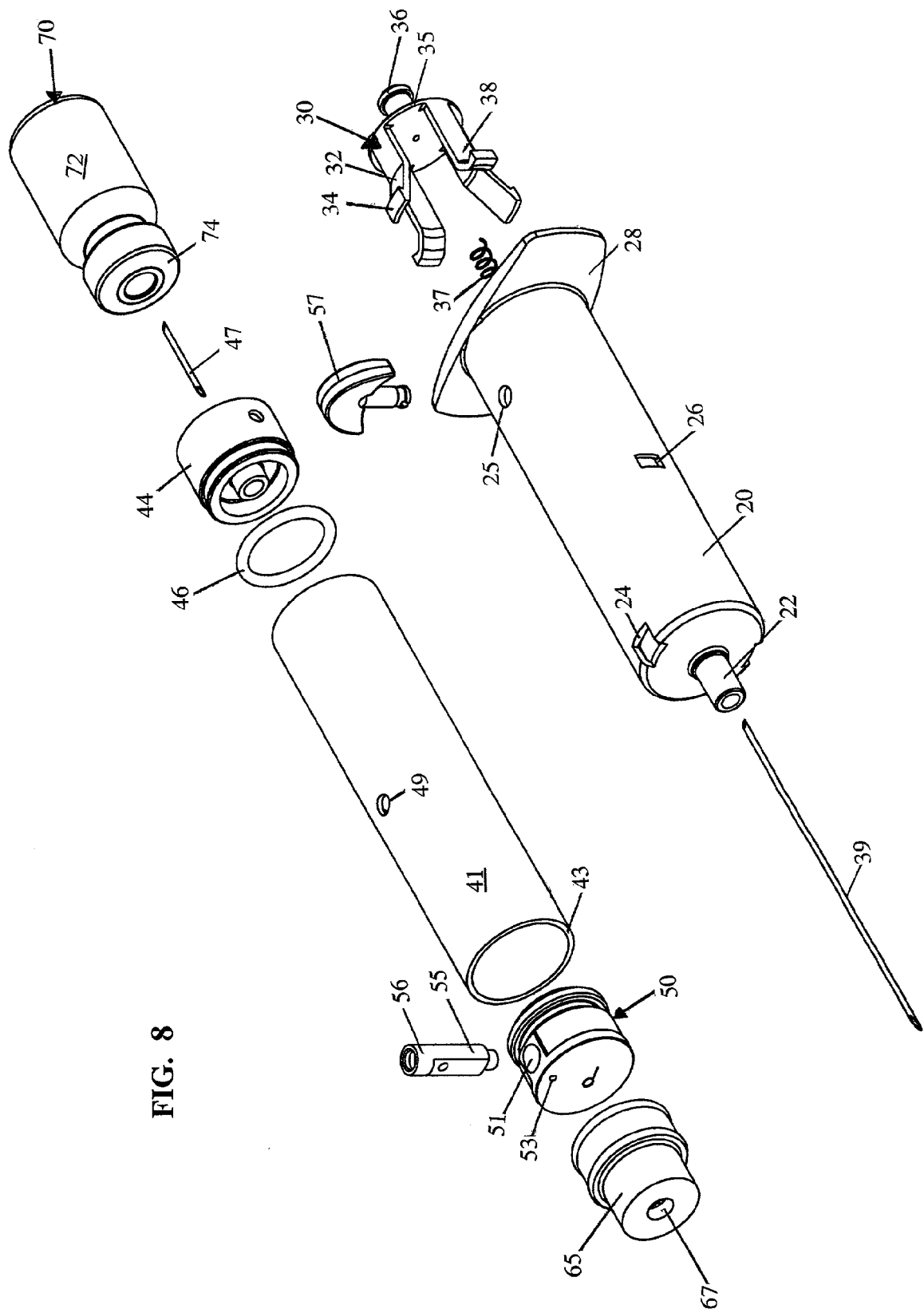
FIG. 8 is an exploded perspective view of the device illustrated in FIG. 1.

Referring now to the drawings in general and to FIG. 1 specifically, a vial injector for injecting fluid from a pre-filled vial is designated 10. The device 10 includes an injection needle 39 having a sharpened tip for piercing a patient. After injection, the injection needle 39 is automatically shielded to prevent inadvertent contact with the contaminated needle.

The device 10 comprises an injector assembly 15 and a vial holder assembly 40. The vial holder 40 holds a vial 70 of medicine, and is attached to the injector assembly 15. The injector assembly 15 has a barrel 20 for receiving the vial holder 40, and a needle hub 35 that carries the injection needle 39.

Referring to FIGS. 1 and 7, the injection needle 39 is a double-ended needle that is operable between two positions, an extended position and a retracted position. In the extended position, the injection needle 39 projects forwardly from the forward end of the barrel 20. In the retracted position, the injection needle is retracted into the barrel so that the forward sharpened tip of the needle is enclosed within the barrel to prevent inadvertent contact with the sharpened tip. When the injection needle 39 is in the extended position, a spring 37 biases the needle rearwardly toward the retracted position. A needle retainer 30 releasably retains the injection needle in the extended position against the bias of the spring. During the injection stroke, the vial holder 40 cooperates with the needle retainer 30 to allow the injection needle to retract into the barrel 20, as shown in FIG. 7.

Some pre-filled injectors utilize a pre-filled cartridge or ampule having a seal or plug that is displaceable to eject medicine from the cartridge or ampule. The present device may be utilized with such cartridges and/or ampules. However, preferably, the present device utilizes a pre-filled vial 70 formed of a container 72 that has fixed walls and a seal 74 that is not displaceable. During use, the medicine is withdrawn from the vial and then expelled.

For instance, referring to FIG. 1, the device 10 comprises a vial holder assembly 40, which has an empty transfer chamber 60 for receiving medicine from the vial. During use, the medicine is drawn out of the vial 70 under negative pressure and into the transfer chamber. The medicine is then ejected from the transfer chamber 60 into the patient.

More specifically, referring to FIGS. 2-4, the medicine from the vial is drawn out of the vial 70 by pushing the vial 70 forwardly to pressurize the fluid in the vial. The pressurized fluid is then transferred into the transfer chamber 60. Any air that is present in the transfer chamber 60 can then be vented as shown in FIGS. 4 and 5. The medicine can then be injected into the patient by driving the vial holder 40 forwardly.

A valve 55 controls the flow of medicine between the vial and the transfer chamber. The valve 55 is a sliding valve that is controlled by pulling the valve. The valve 55 has a port that is slidable within a transfer seal 50 in the vial assembly. In the open position, the valve aligns with a fluid passage 52 in the transfer seal 50, as shown in FIG. 3, so that fluid can flow from the vial into the transfer chamber 60. After the fluid is transferred into the transfer chamber 60, the valve 55 is pulled into the closed position so that the fluid passage is blocked to prevent the medicine from leaking back into the vial 70 during the injection stroke.

To inject the medicine, the vial 70 and vial holder 40 are driven forwardly to expel the medicine from the transfer chamber 60. At the end of the injection, the forward end of the vial assembly 40 engages the needle retainer 30 thereby releasing the needle 39 for retraction, as shown in FIG. 6. The spring 37 then displaces the needle rearwardly so that the contaminated needle is shielded within the barrel 20, as shown in FIGS. 7.

Injector Assembly

Referring now to FIG. 1, the elements of the injector assembly 15 will be described in greater detail. The injector assembly 15 comprises a barrel 20 and a needle retainer 30 releasably retaining the injection needle 39. A needle hub 35 attached to the needle retainer 30 has a mounting stem 36 for attaching the vial holder 40 to the injector assembly 15.

As shown in FIGS. 1 and 8, the barrel 20 is generally cylindrical and the distal end of the barrel has a tapered nose 22. The nose 22 has an opening through which the injection needle 39 extends so that the sharpened forward tip of the needle can be inserted into a patient. The rearward end of the barrel 20 is open, forming a cylindrical socket adapted to receive the vial holder 40. Two laterally extending flanges 28 project outwardly from the barrel 20, transverse the longitudinal axis of the barrel, forming a pair of finger grips for operating the device 10. The barrel 20 further includes a pair of retaining apertures 24 and a pair of lockout windows 26 that cooperate with the needle retainer 30 as described further below. In addition, the barrel 20 has a post hole 25 that extends through opposing sidewalls. The post holes 25 cooperates with the valve 55 to releasably lock the injector assembly 15 with the vial holder assembly 40, as discussed further below.

The needle hub 35 is a generally cylindrical element having a central bore. The injection needle 39 is disposed within the central bore of the hub 35 so that the rearward end of the needle projects rearwardly from the hub and the forward end of the needle projects forwardly from the hub. The needle 39 can be attached to the hub 35 in one of several ways. For example, the needle 39 can be attached to the hub 35 by an adhesive such as a UV curable adhesive. Alternatively, the needle 39 can be molded into the hub 35, which is formed of plastic. The rearward end of the hub 35 includes a mounting stem 36 in the form of a barbed connector configured to cooperate with the vial holder 40 to connect the vial holder to the needle hub 35 as discussed further below.

The needle retainer 30 is attached to the needle hub 35, and preferably is integrally molded with the needle hub as a single piece. The needle retainer 30 is preferably molded out of a rigid, high strength resin, such as polycarbonate. Prior to retraction, the needle retainer 30 maintains the needle hub 35 and attached needle 39 in a fixed axial position while the medication is expelled from the vial holder 40. After the injection, the needle retainer 30 releases the needle hub 35 and the attached needle 39, which are displaced rearwardly by a compression spring 37.

The spring 37 is a compression spring and may be formed of stainless steel, treated carbon steel wire or other suitable non-corrosive spring metal. The residual compression of the spring prior to disengagement of the needle retainer is of sufficient magnitude to facilitate complete needle retraction and overcome the frictional resistance between sliding components within the device 10.

Referring again to FIGS. 1 and 8, the needle retainer 30 includes a pair of retaining arms 32 that extend radially outwardly and forwardly from the distal end of the needle retainer 30. During operation, the needle retainer 30 is operable between a locked position and an unlocked position. In the locked position, the retaining arms 32 engage the retaining apertures 24 in the barrel wall to maintain the needle in a fixed axial position with the forward tip of the injection needle 39 projecting forwardly from the barrel 20. More specifically, in the locked position, the retaining arms 32 engage the barrel 20 to hold the needle hub 35 and needle 39 against the rearward bias of the spring 37. In the unlocked position, the retaining arms 32 are positioned so as to allow the needle hub 35 and needle 39 to be retracted rearwardly, as shown in FIG. 6. More specifically, in the unlocked position, the retaining arms 32 are disengaged from the retaining apertures 24, allowing the spring 37 to propel the needle hub 35 and needle 39 rearwardly as shown in FIG. 7.

Referring to FIG. 1, as discussed above, the retaining arms 32 on the needle retainer 30 project forwardly and outwardly into engagement with the retaining apertures 24 in the wall of the barrel 20. The terminal end of each arm forms a retaining tab 34 that is configured to project into a retaining aperture 24. More specifically, the retaining tabs 34 engage the lip formed by each retaining aperture 24 in the wall of the barrel 20. In this way, the retaining tabs 34 operate as a pair of latches to retain the needle hub 35 and the injection needle 39 against the rearward bias of the spring.

As shown in FIG. 7, when the injection needle 39 is retracted, the needle, needle retainer 30 and vial holder 40 are displaced rearwardly together. Preferably, the injection device 10 includes a mechanism for limiting rearward displacement of the retracted elements. Specifically, as shown in FIG. 7, the injector assembly 15 preferably includes a pair of guide arms 38 that cooperate with a pair of lockout windows 26 in the barrel 20 to lock the retracted elements in the retracted position after use.

The guide arms 38 cooperate with a pair of alignment channels or grooves formed in the interior wall of the barrel 20. The guide arms 38 may be molded out of a rigid, resilient high strength resin, such as polycarbonate. The guide arms 38 extend forwardly from the needle hub 35 and project radially outwardly into engagement with the alignment grooves.

Each guide arm 38 includes a linear elongated rear portion which preferably is generally parallel to the longitudinal axis of barrel 20. The forward portion of each guide arm 38 bends outwardly transverse the longitudinal axis of the barrel 20 and extends into one of the alignment grooves. When the needle retainer 30 is disposed within the barrel, the guide arms 38 are deflected radially inwardly from their natural state. In this position, the guide arms 38 are biased radially outwardly against the inner wall of the barrel 20 due to the resilient properties of the guide arms.

The forward ends of guide arms 38 are contained within the alignment grooves to substantially limit rotation of the needle and needle retainer 30 during needle retraction. This engagement ensures that the guide arms are aligned with the lockout windows 26 so that the guide arms snap into the lockout windows at the end of retraction. In this way, the needle retainer 30 is limited to axial displacement during needle retraction. During retraction, the frictional resistance between the forward ends of the guide arms 38 and the inside wall of the barrel 20 is overcome by the expansion force of the spring 37.

As shown in FIG. 7, the linear elongated rear portion of each guide arm 38 is spaced radially inwardly from the inner wall of the barrel 20 to create a clearance space between the linear portion of the guide arms and the barrel. Preferably, the minimum radial thickness of the clearance space is greater than the thickness of the wall of the vial assembly housing 41. In this way, when the vial holder 40 is advanced forwardly to disengage the retaining arms 32, the vial holder does not engage the guide arms 38 which could otherwise prevent the guide arms from locking in the lockout windows 26 at the end of retraction.

Each alignment groove is substantially parallel to the longitudinal axis of the barrel 20. The groove may extend to the rearward end of the barrel. However, it may be desirable to terminate the groove forward of the rearward end of the barrel. The rearward portion of each alignment groove intersects a lockout window 26 formed in the wall of the barrel 20. The lockout windows 26 are adapted to receive the forward ends of the guide arms 38, as shown in FIG. 7. In particular, as the front end of each guide arm 38 aligns with the corresponding lockout window 26 during needle retraction, the radially outward bias of the guide arm displaces the arm outwardly so that the forward end projects into the lockout window. The engagement between the guide arms 38 and lockout windows 26 prevent further axial movement of the injection needle 39. As a result, the retracted elements are limited from further displacement in the forward or rearward direction.

Referring now to FIGS. 5-7 the automatic retraction of the injection needle 39 shall be described. The vial holder 40 is axially advanced to the proximal end of the barrel 20 until the medication is completely expelled from the transfer chamber 60 as shown in FIGS. 5 and 6. As the vial holder 40 is advanced, the forward rim 43 of the housing 41 is displaced into engagement with the retaining arms 32 of needle retainer 30.

After the rim 43 of the vial holder housing 41 engages the retaining arms 32, continued axial advancement of the vial holder deflects the retaining arms radially inwardly so that the retaining tabs 34 are displaced inwardly, as shown in FIG. 6. In the inward position, the retaining tabs 34 are disengaged from the retaining apertures 24 of the barrel 20. In this way, the vial holder 40 operates as an actuator, such that axial advancement of the vial holder assembly displaces the needle retainer 30 into an unlocked position. In the unlocked position, the needle retainer 30 is no longer locked in place against the force of the spring 37. After the needle retainer 30 is in the unlocked position and the user releases pressure on the vial holder 40, the spring 37 propels the needle 39 rearwardly until the sharpened distal tip of the needle is enclosed within the barrel 20.

Vial Holder Assembly

Referring to FIG. 1, the details of the vial holder assembly 40 will be described in detail. The vial holder 40 comprises an elongated hollow housing 41. The housing 41 comprises three seals. A front seal 65 seals the forward end of the housing 42, and a slidable vial carrier 44 seals the rearward end of the housing. The third seal is a transfer seal 50 disposed between the front seal 65 and the carrier 44 which separates the housing into two chambers: (1) a transfer chamber 60 between the front seal 65 and the transfer seal; and (2) an air-pump chamber 48 between the vial carrier and the transfer seal. The transfer seal 50 is pierceable to allow fluid transfer between the vial 70 and the transfer chamber, as described further below. A valve 55 in the transfer seal 50 is operable to reseal the transfer seal to prevent leakage of fluid from the transfer chamber back into the vial 70.

The vial carrier 44 includes a double-ended transfer needle 47. The rearward end of the transfer needle 47 projects into the socket in the vial carrier 44 to pierce the septum 72 on the vial. Preferably, the length of the transfer needle projecting into the carrier socket is slightly longer than the thickness of the vial septum. In this way, the heel of the needle bevel is spaced from the inner edge of the septum a short distance which preferably is less than the length of the needle bevel.

The front seal 65 cooperates with the barbed connector 36 on the needle hub 35 to attach the vial holder assembly 40 to the injector assembly 15. The front seal 65 is an elastomeric seal, which may be molded in a self-sealing biocompatible elastomer such as polyisoprene. The front seal 65 is generally cylindrical, having a plurality of axially-spaced circumferential ribs. The ribs, frictionally and sealingly engage the interior of the housing 41 to provide a fluid tight seal, thereby preventing fluid from leaking from the vial holder 40. The front seal 65 also has a wall that is pierceable by the rearward sharpened tip of the injection needle 39. After being pierced, the front end of the front seal 65 reseals around the needle 39 to prevent fluid from leaking from the transfer chamber 60.

Referring now to FIG. 1 the front seal 65 has a socket 67 configured to cooperate with the barbed connector 36 on the needle hub 35. The socket 67 includes two radially relieved recesses that mate with the barbed connector 36. Specifically, the barbed connector 36 matingly engages the front seal 65 in a first position and a second position.

In the first position, the barbed connector 36 engages the first recess, as shown in FIG. 1. In this position, the vial is attached to the hub, but the rearward end of the needle does not pierce the front seal 65. Displacing the vial holder assembly forwardly relative to the needle hub 35, displaces the forward seal over the barb into the second position. In the second position, the barbed connector 36 engages the second recess, as shown in FIG. 4. In this position, the rearward end of the injection needle 39 pierces the front seal 65.

The front seal 65 includes an elongated hollowed socket 67 in which the rearward end of the needle projects. The rearward end of the socket 67 is sealed by a pierceable wall. As shown in FIG. 1 prior to use, the front seal 65 is mounted in the first position so that the barbed connector 36 engages the first recess. In this position, the injection needle 39 does not penetrate the pierceable wall in the forward seal. As the vial holder assembly 40 is displaced forwardly, the barbed connector 36 engages the second recess in the front seal 65, and the rearward end of the injection needle 39 pierces the wall so that the needle is in fluid communication with the transfer chamber 60. After the injection needle 39 penetrates the pierceable wall, the wall reseals around the needle to form a fluid-tight seal and prevent medication in the vial holder 40 from leaking around the needle.

The connection between the front seal 65 and the needle hub 35 is preferably a one-way engagement. In other words, when the front seal 65 is mounted on the barbed connector 36, the vial holder 40 can be displaced forwardly relative to the barbed connector, but the front seal cannot be displaced rearwardly relative to the barbed connector. In this way, the vial holder 40 cannot be readily removed from the needle hub 35 in the barrel 20.

The one-way connection is facilitated by the rearward-facing tapered shoulder of the barbed connector 36 and the square shaped forward-facing shoulder of the recesses in the forward seal 65. In particular, the rearward-facing shoulder of the barbed connector 36 cooperates with tapered sides in the first and second radial recesses to permit relative displacement of the plug from the first recess to the second recess. Reverse displacement from the second recess back to the first recess is resisted by the square shaped forward-facing shoulders on barbed connector 36, which act to impede reverse displacement.

Referring to FIG. 1, the rearward end of the vial holder housing 41 is sealed by the vial carrier 44. The vial carrier is a cylindrical element, having a circumferential groove around its exterior, into which a carrier seal 46 is seated. The carrier seal 46 is an elastomeric seal, such as an o-ring, that forms a fluid-tight seal between the vial carrier 44 and the interior wall of the vial holder housing 41. In addition, the carrier seal 46 provides a sliding seal so that the vial carrier 44 can slide within the housing 41, while maintaining an air-tight seal with the interior wall of the housing. This sliding seal allows the vial carrier 44 to operate as a piston to pump air into the vial 70 as described further below.

The rearward end of the vial carrier 44 is open, forming a socket configured to cooperate with and receive a vial 70. Specifically, the socket is adapted to receive the head of a vial, as shown in FIG. 1, so that preferably there is a light interference fit between the head of the vial and the interior of the socket. In this way, the vial carrier 44 grips the vial to secure the vial in the vial carrier. Preferably, the vial carrier 44 cooperates with an annular ridge 42 formed in the interior of the housing 41. The ridge 42 forms an interference fit with the vial carrier to prevent axial displacement of the carrier 44 when the vial 70 is inserted into the carrier. However, the interference of the ridge is light enough that the carrier 44 can be axially advanced by pressing the vial and carrier forwardly after attachment. In other words, preferably, the frictional force of the ridge interference is only slightly greater than the force necessary to puncture the septum and insert the vial into the carrier.

The forward end of the vial carrier forms a wall having a reduced diameter opening. A transfer needle 47 projects through the reduced diameter opening in the forward wall. Preferably, the transfer needle 47 is a double-ended needle, and the rearward end of the transfer needle projects rearwardly into the socket to pierce the septum 74 on the vial. Further, preferably, the length of the transfer needle 47 projecting from the forward wall into the socket is slightly longer than the thickness of the septum 74. In this way, the heel of the bevel of the rearward end of the transfer needle is either aligned with the inner surface of the septum 74 or spaced from the inner surface of the septum a short distance. The forward end of the transfer needle 47 projects forwardly from the vial carrier 42 and is operable to pierce the transfer seal 50, as discussed further below.

As shown in FIGS. 1 and 2*a*, the transfer seal 50 is disposed in the vial holder housing 41 between the vial carrier 44 and the front seal 65, thereby dividing the housing into the forward transfer chamber 60 and the rearward air-pump chamber 48. The transfer seal 50 is an elastomeric seal that forms a fluid-tight seal with the interior wall of the housing 41. A circumferential groove around the exterior of the transfer seal 50 cooperates with an annular flange on the interior of the housing 41 to connect the transfer seal to the housing. The groove and the flange cooperate to fix the axial position of the transfer seal relative to the housing to prevent the transfer seal from sliding within the housing.

Referring to FIG. 2*a*, the transfer seal 50 comprises a fluid path 52 that extends axially through the transfer seal, and terminates at a rearward wall of the transfer seal. This rearward wall forms a pierceable seal that seals the fluid path 52 to prevent transfer of air or liquid between the air pump chamber 48 and the transfer chamber 60. As discussed further below, during use, the transfer needle 47 pierces the rearward wall of the transfer seal 50, extending into the fluid path 52, so that fluid flows from the vial 70, through the transfer needle and the fluid path, and into the transfer chamber.

A valve 55 is located in the transfer seal to control the flow of fluid between the transfer chamber and the vial 70 after the medicine is transferred from the vial to the transfer chamber 60. More specifically, the transfer seal 50 comprises a valve chamber 51 (see FIG. 8) disposed transverse the fluid path 52. The valve is a sliding valve 55 that forms a fluid-tight seal with the valve chamber in the transfer seal 50. The valve 55 has a hole through its side. When the valve 55 is in the open position (see FIG. 2*a*), the side hole in the valve 55 aligns with the fluid path 52 in the transfer seal 50 to allow fluid to flow from the vial into the transfer chamber. The valve 55 is closed by pulling the valve so that the valve slides within the valve chamber until the side hole in the valve seals against the transfer seal 50 as shown in FIG. 4*a*. In the closed position, the valve 55 prevents fluid from flowing from the transfer chamber 60 back into the vial 70. As shown in FIG. 8, the valve 55 has two flats that register with the valve chamber, which keeps the valve from rotating within the valve chamber so that the hole through the valve aligns with the fluid path 52 in the transfer seal 50.

Referring again to FIGS. 2*a* and 8, a detachable pull pin 57 is attached to the first end of the valve 55. The pull pin 57 projects through one of the post holes 25 in the injector barrel 20 and through one of the locking holes 49 in the vial holder housing 41. The second end of the valve 55 projects through the other locking hole 49 in the housing and the other post hole 25 in the barrel 20. In this way, when the valve is disposed in the open position, the valve 55 and pull pin 57 cooperate to releasably lock the barrel 20 and the housing 41 together to prevent axial displacement of the vial holder assembly 40 relative to the injector assembly 15.

Referring to FIGS. 4*a* and 8, when the valve is displaced to the closed position, the second end of the valve 55 is drawn inwardly, out of engagement with the post hole 25 in the barrel 20, and out of engagement with the locking hole 49 in the housing 41. In addition, by detaching the pull pin after closing the valve, the pull pin is pulled out of engagement with the barrel 20 and the housing 41, so that the vial holder assembly 40 is displaceable relative to the injector assembly 15.

The first end of the valve 55 forms an enlarged head 56 having a socket for receiving the end of the pull pin 57 The pull pin 57 engages the socket in the enlarged head 56 of the valve, forming an interference or snap-fit. The frictional force between the pull pin 57 and the valve head 56 is greater than the frictional force between the valve 55 and the valve chamber 51 in the transfer seal 50. In this way, pulling on the pull pin 57 slides the valve 55 from the open position to the closed position. When the valve is closed, the head 56 of the valve stops against the interior wall of the vial holder housing 41. Continuing to pull on the pull pin 57 detaches the pull pin from the valve 55.

Referring to FIGS. 2*a* and 4*a*, the transfer seal 50 includes a vent hole 53 for venting air from the transfer chamber 60 when fluid is transferred from the vial 70 into the transfer chamber. The vent hole 53 is open when the valve is open, as shown in FIG. 2*a*. When the valve 55 is pulled into the closed position, the enlarged head 56 of the valve seals the vent hole 53 to prevent medicine from leaking out the vent hole, as shown in FIG. 4*a*.

Method of Operation

Before describing the details of operation, a short summary is provided. First, the vial 70 is inserted into the vial holder 40 so that the transfer needle 47 pierces the septum 74 on the vial (see FIG. 1). Air is pumped into the vial 70 from the air pump chamber 48 to pressurize the vial (see FIG. 2). The transfer needle 47 then pierces the transfer seal 50, and the pressurized medicine in the vial flows into the transfer chamber 60 (see FIG. 3). The valve 55 is then pulled closed (see FIG. 4). Air is then purged from the transfer chamber 60 and the medicine is injected into the patient by driving the vial holder 40 forwardly (see FIGS. 5 and 6). At the end of the injection stroke, the forward rim 43 of the vial holder assembly 40 engages the needle retainer 30, displacing the needle retainer arms 32 inwardly (see FIG. 6). The spring 37 then displaces the needle hub 35 and needle 39 rearwardly, along with the vial holder assembly 40 (see FIG. 7). At the end of retraction, the locking arms 38 engage the lockout windows 26 to lock the needle in the retracted position. The shielded device 10 can then be disposed of safely.

The operation of the device 10 will now be described in detail. Prior to use, the air pump chamber 48 and the transfer chamber 60 are empty. Referring to FIG. 1, the vial 70 is inserted into the rearward end of the vial holder 40 so that the head of the vial seats in the vial carrier 44 and the rearward end of the transfer needle 47 pierces the septum 74 on the vial. When the vial 70 is inserted into the needle carrier 44, the interference between the vial carrier 44 and the ridge 42 in the housing 41 is greater than the force required to pierce the septum, so that the ridge retains the vial carrier in place prior to piercing the septum.

After the transfer needle 47 pierces the septum 74, the vial 70 is displaced forwardly, which in turn displaces the vial carrier 44 forwardly into the air-pump chamber 48. Since the carrier seal 46 forms a fluid-tight seal with the interior of the housing, displacing the carrier 44 forwardly pumps the air from the air pump chamber 48 into the vial 70, which pressurizes the vial, as shown in FIG. 2.

At the end of the pressurizing stroke, the forward tip of the transfer needle 47 pierces the transfer seal 50 so that the transfer needle projects into the fluid path 52 in the transfer seal. The transfer seal reseals around the transfer needle 47 to prevent medicine from leaking out of the transfer chamber around the needle. At this point, the vial is in fluid communication with the transfer chamber. Since the device is held with the vial down, the medicine from the pressurized vial flows downwardly into the transfer chamber, as shown in FIG. 3. In addition, since the heel of the rearward tip of the needle is adjacent the inner surface of the septum, substantially all of the medicine can flow out of the vial and into the transfer chamber. As the fluid flows into the transfer chamber 60, air in the transfer chamber vents out the vent hole 53 to prevent fluid from getting line-locked in the vial.

FIG. 3 illustrates the device such that at the end of the pressurization stroke, the rearward end of the vial 70 protrudes from the rearward end of the vial holder 40. Alternatively, and preferably, the holder is configured so that the length of the housing 41 rearward of the transfer seal 50 is substantially at least as long as the length of the vial carrier 44 and the attached vial 70. In this way, at the end of the pressurization stroke, the rearward end of the vial is either disposed within the housing 41 or is substantially flush with the rearward end of the housing, so that the vial cannot be readily removed from the holder.

After the medicine is transferred into the transfer chamber, the pull pin 57 is pulled, which in turn displaces the valve 55 sideways into the closed position, sealing off the fluid path 52 in the transfer seal. At the same time, the head 56 of the valve is displaced over the vent hole 53 to seal the vent hole. Continuing to pull on the pull pin 57 detaches the pull pin from the valve 55. At this point, the valve 55 and pull pin 57 are disengaged from the post holes 25 in the barrel and the locking holes 49 in the vial holder housing 41, so that the vial holder 40 can be displaced relative to the injector assembly 15. In addition, at this point, the fluid is sealed in the transfer chamber 60 between the transfer seal 50 and the front seal 65.

As shown in FIG. 4, after the valve 55 is closed, the device is flipped vertically so that the needle is directed upwardly. The vial holder assembly 40 is then displaced forwardly in the barrel 20 (i.e. upwardly) so that the front seal moves forwardly, and the barbed connector pops into the second recess in the front seal socket 67. In doing so, the rearward tip of the injection needle 39 pierces the front seal 65 so that the injection needle is in fluid communication with the transfer chamber 60. Once the barbed connector 36 engages the second socket in the front seal 65, the needle hub maintains the front seal at a fixed axial position as the vial holder 40 is displaced forwardly.

Any air in the transfer chamber is purged by displacing the vial holder 40 forwardly over the front seal while holding the device 10 with the needle upwardly. After the air is purged, the device is ready to inject, as shown in FIG. 5. The forward sharpened tip of the injection needle 39 may then be inserted into the patient, and the medicine is injected into the patient by driving the vial holder housing 41 forwardly.

Displacing the vial holder assembly 40 forwardly relative to the injection assembly 15 drives the housing 41 over the axially fixed front seal 65, thereby expelling the medicine from the transfer chamber. At the end of the injection stroke, the forward rim of the housing 41 engages the arms 32 of the needle retainer 30, displacing the arms radially inwardly, as shown in FIG. 6. At this point, the injection needle 39 is released for retraction. As soon as the operator releases pressure against the rearward end of the vial holder assembly 40, the spring 37 displaces the needle hub 35 and attached needle rearwardly, along with the vial assembly.

As the injection needle 39 is retracted, the guide arms 38 ride in the guide slots in the interior of the barrel, until the ends of the guide arms reach the lockout windows 26. At this point, the guide arms resiliently displace outwardly into the lockout windows 26, thereby locking the needle hub 35 and attached needle 39 in the retracted position. In this way, the sharpened tip of the contaminated needle is automatically protected against inadvertent contact after use, and can be safely disposed of, preferably in a sharps container.

Referring now to FIGS. 9-22, an alternate embodiment of a vial injector for injecting fluid from a prefilled vial is designated 110. The device 110 includes a needle 112 having a sharpened tip for piercing a patient. After injection, the needle 112 is automatically shielded to prevent inadvertent contact with the contaminated needle.

Referring to FIGS. 10 and 12, the device includes a double-ended needle 112 projecting forwardly from a generally cylindrical barrel 130. A compression spring 126 biases the needle 112 rearwardly. A needle retainer 120 releasably retains the needle against the bias of the spring 126.

The needle 112 is operable between two positions, an extended position and a retracted position. In the extended position, the needle 112 projects forwardly from the forward end of the barrel 130. In the retracted position, the needle is retracted into the barrel so that the forward sharpened tip of the needle is enclosed within the barrel to prevent inadvertent contact with the sharpened tip. When the needle is in the extended position, the spring 126 biases the needle 112 rearwardly toward the retracted position. The needle retainer 120 releasably retains the needle into the extended position against the bias of the spring. During the injection stroke, the vial assembly 150 cooperates with the needle retainer 120 to allow the needle to retract into the barrel 130, as shown in FIGS. 20-22.

Some prefilled injectors utilize a prefilled vial or ampoule having a seal or plug that is displaceable within the vial to eject medicine from the vial. The device 110 may be configured to utilize such cartridges and/or vials. However, preferably, the device 110 utilizes a prefilled vial 90 that utilizes fixed walls and a seal that is not displaceable. During use the medicine is withdrawn from the vial and then expelled.

For instance, referring to FIG. 14, the device 110 comprises a vial assembly 150, which has an empty transfer chamber 155 for receiving medicine from the vial. During use, the medicine is drawn out of the vial 190 and into the transfer chamber. The medicine is then ejected from the transfer chamber 155 into the patient.

More specifically, referring to FIG. 15, the medicine from the vial is drawn out of the vial 190 by pulling the vial assembly 150 rearwardly to create a vacuum that draws the fluid out of the vial and into the transfer chamber 155. Any air that is present in the transfer chamber 155 can then be vented as shown in FIG. 15. The medicine can then be injected into the patient by driving the vial assembly 150 forwardly.

Figure 19:
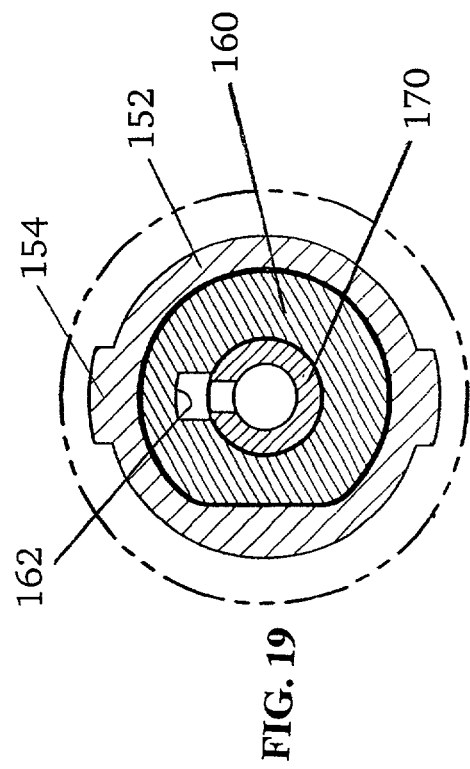
FIG. 19 lesson is a cross-sectional view of the portion of the device illustrated in FIG. 18 designated Detail 19.
Figure 18:
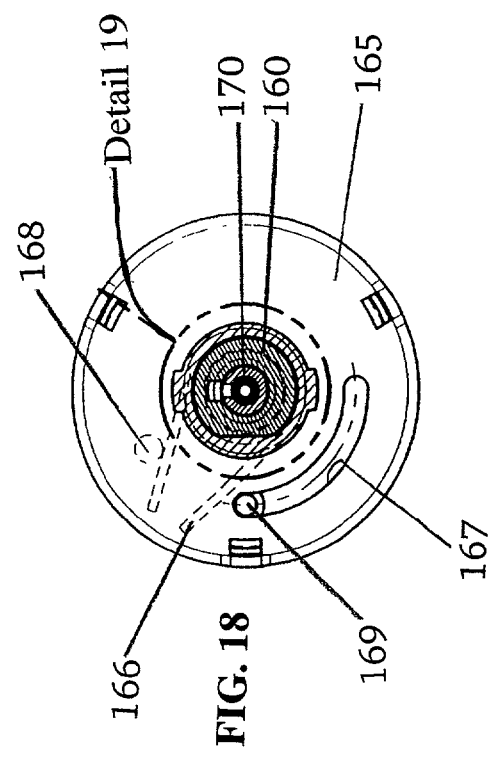
FIG. 18 is a cross-sectional view of the device illustrated in FIG. 13, taken along the line 18-18.
Figure 17:
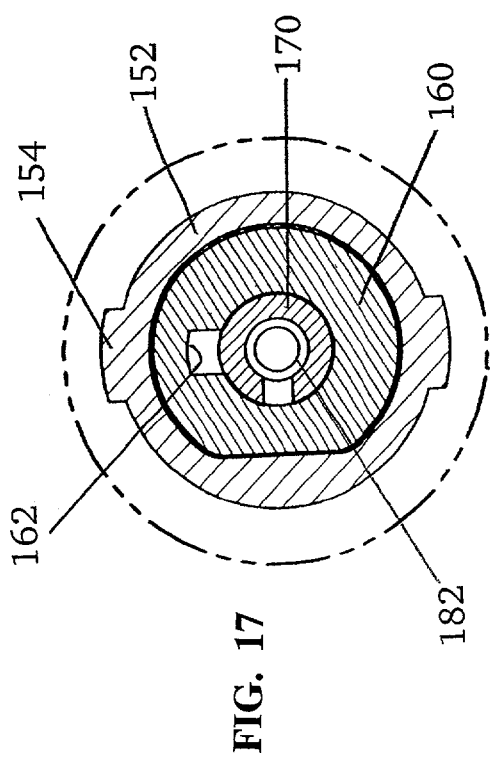
FIG. 17 is a cross-sectional view of the portion of the device illustrated in FIG. 16 designated Detail 17.
Figure 16:
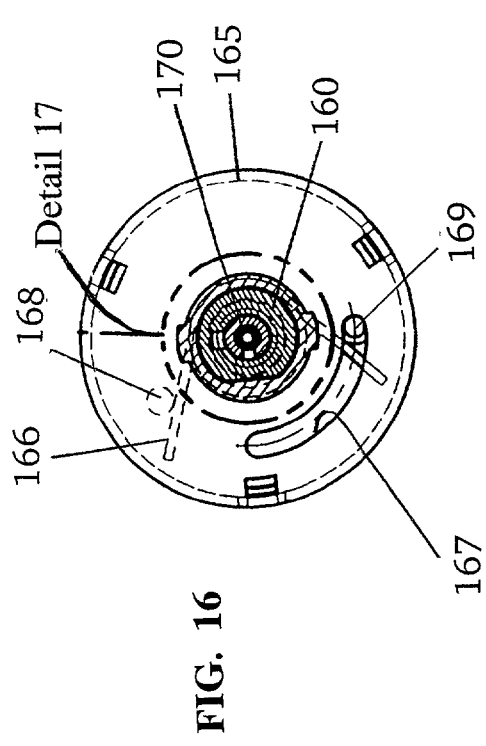
FIG. 16 is a cross-sectional view of the device illustrated in FIG. 12, taken along the line 16-16.

A valve 170 controls the flow of medicine from the vial into the transfer chamber. The valve 170 is a rotary valve that is controlled by twisting the valve. The valve 170 has a port that is rotatable within a rearward seal 160 in the vial assembly. In a closed position, the valve seals 170 against the rearward seal 160 in the vial assembly, as shown in FIG. 17. When the valve 170 is closed, the medicine cannot flow from the vial 190 into the transfer chamber 155. In the open position, the valve aligns with a fluid passage 162 in the rear seal 160, as shown in FIG. 19. Fluid can then flow from the vial into the transfer chamber 155 by pulling the vial assembly 150 rearwardly. After the fluid is transferred into the transfer chamber 155, the valve 170 is twisted back into the closed position to prevent the medicine from leaking back into the vial 190 during the injection stroke.

At the end of the injection, the forward end of the vial assembly engages the needle retainer 120 thereby releasing the needle 112 for retraction, as shown in FIG. 20. The spring 126 then displaces the needle rearwardly so that the contaminated needle is shielded within the barrel 130, as shown in FIGS. 21 and 22.

Needle Assembly

Referring now to FIGS. 10-12, the elements of the injector device 110 will be described in greater detail. The injector 110 comprises a needle assembly 115 and a vial assembly 150. The needle assembly 115 comprises a barrel 130 and a needle retainer 120 releasably retaining the needle 112. Inside the barrel is a needle hub 121 having a mounting stem 125 for attaching the vial assembly 150 to the needle assembly 115.

The barrel 130 is generally cylindrical and the distal end of the barrel has a tapered nose 132. The nose 132 has an opening through which the needle 112 extends so that the sharpened forward tip of the needle can be inserted into a patient. The rearward end of the barrel 130 is open, forming a cylindrical socket adapted to receive the vial assembly 150. Two laterally extending flanges 136 project outwardly from the barrel 130, transverse the longitudinal axis of the barrel, forming a pair of finger grips for operating the device 110. The barrel 130 further includes a pair of retaining apertures 138 and a pair of lockout windows 139 that cooperate with the needle retainer 120 as described further below.

Needle Retainer

As shown in FIG. 12, the needle hub 121 is integrally attached to the rearward end of the needle retainer 120. The needle hub 121 is a generally cylindrical element having a central bore. The needle 112 is disposed within the central bore of the hub 121 so that the rearward end of the needle projects rearwardly from the hub and the forward end of the needle projects forwardly from the hub. The needle 112 can be attached to the hub 121 in one of several ways. For example, the needle 112 can be attached to the hub 121 by an adhesive such as a UV curable adhesive. Alternatively, the needle 112 can be molded into the hub 121, which is formed of plastic. The rearward end of the hub 121 includes a circumferentially barbed connector 125 configured to cooperate with the vial assembly 150 to connect the vial assembly to the needle hub 121 as discussed further below.

The needle retainer 120 is axially displaceable within barrel 130 to facilitate needle retraction. The needle retainer 120 can be molded out of a rigid, high strength resin, such as polycarbonate. Prior to retraction, the needle retainer 120 is maintained in a fixed axial position while the medication is expelled from the vial assembly 150. After the injection, the needle retainer 120 and the attached needle 112 are displaced rearwardly by a compression spring 126.

The spring 126 is a compression spring and may be formed of stainless steel, treated carbon steel wire or other suitable non-corrosive spring metal. The residual compression of the spring prior to disengagement of the needle retainer is of sufficient magnitude to facilitate complete needle retraction and overcome the frictional resistance between sliding components within the device 110.

Referring now to FIGS. 10 and 12, the needle retainer 120 includes a pair of retaining arms 122 that extend radially outwardly and forwardly from the distal end of the needle retainer 120. During operation, the needle retainer 120 is operable between a locked position and an unlocked position. In the locked position, the retaining arms 122 engage the retaining apertures 138 in the barrel wall to maintain the needle in a fixed axial position with the forward tip of needle 112 projecting forwardly from the barrel 130. More specifically, in the locked position, the retaining arms 122 engage the barrel 130 to hold the needle hub 121 and needle 112 against the rearward bias of the spring 126. In the unlocked position, the retaining arms 122 are positioned so as to allow the needle hub 121 and needle 112 to be retracted rearwardly. More specifically, in the unlocked position, the retaining arms 122 are disengaged from the retaining apertures 138, allowing the spring 126 to propel the needle hub 121 and needle 112 rearwardly.

As discussed above, the retaining arms 122 on the needle retainer 120 project forwardly and outwardly into engagement with the retaining apertures 138 in the wall of the barrel 130. The terminal end of each arm forms a retaining tab 124 that is configured to project into a retaining aperture 138. More specifically, the retaining tabs 124 engage the lip formed by each retaining aperture 138 in the wall of the barrel 130. In this way, the retaining tabs 124 operate as a pair of latches to retain the needle hub 121 and needle 112 against the rearward bias of the spring.

Rearward Lock

As shown in FIG. 22, when the needle 112 is retracted, the needle, needle retainer 120 and vial assembly 150 are displaced rearwardly together. Preferably, the injection device 110 includes a mechanism for limiting rearward displacement of the retracted elements. Referring now to FIGS. 10 and 22, the needle assembly 115 includes a pair of guide arms 128 that cooperate with a pair of lockout windows 139 in the barrel 130 to lock the retracted elements in the retracted position after use.

The guide arms 138 cooperate with a pair of alignment channels or grooves formed in the interior wall of the barrel 130. The guide arms 128 may be molded out of a rigid, resilient high strength resin, such as polycarbonate. The guide arms 128 extend forwardly from the needle hub 121 and project radially outwardly into engagement with the alignment grooves.

Each guide arm 128 includes a linear elongated rear portion which preferably is generally parallel to the longitudinal axis of barrel 130. The forward portion of each guide arm 128 bends outwardly transverse the longitudinal axis of the barrel 130 and extends into one of the alignment grooves. When the needle retainer 120 is disposed within the barrel, the guide arms 128 are deflected radially inwardly from their natural state. In this position, the guide arms 128 are biased radially outwardly against the inner wall of the barrel 130 due to the resilient properties of the guide arms.

The forward ends of guide arms 128 are contained within the alignment grooves to substantially limit rotation of the needle and needle retainer 120 during needle retraction. This engagement ensures that the guide arms are aligned with the lockout windows 139 so that the guide arms snap into the lockout windows at the end of retraction. In this way, the needle retainer 120 is limited to axial displacement during needle retraction. During retraction, the frictional resistance between the forward ends of the guide arms 128 and the inside wall of the barrel 130 is overcome by the expansion force of the spring 126.

As shown in FIG. 22, the linear elongated rear portion of each guide arm 128 is spaced radially inwardly from the inner wall of the barrel 130 to create a clearance space between the linear portion of the guide arms and the barrel. Preferably, the minimum radial thickness of the clearance space is greater than the thickness of the wall of the vial assembly housing 152. In this way, when the vial assembly 150 is advanced forwardly to disengage the retaining arms 122, advancement of the vial assembly is not impeded by the guide arms 128.

Each alignment groove is substantially parallel to the longitudinal axis of the barrel 130. The groove may extend to the rearward end of the barrel. However, it may be desirable to terminate the groove forward of the rearward end of the barrel. The rearward portion of each alignment groove intersects a lockout window 139 formed in the wall of the barrel 130. The lockout windows 139 are adapted to receive the forward ends of the guide arms 128, as shown in FIG. 22. In particular, as the front end of each guide arm 128 aligns with the corresponding lockout window 139 during needle retraction, the radially outward bias of the guide arm displaces the arm outwardly so that the forward end projects into the lockout window. The engagement between the guide arms 128 and lockout windows 139 prevent further axial movement of the retainer 122. As a result, the retracted elements are limited from further displacement in the forward or rearward direction.

The injection device 110 may also include a mechanism to limit tampering or removal of the vial assembly 150 from the needle assembly 115. Specifically, the rearward end of the barrel 130 may include an annular lip that projects radially inwardly from the inside wall of the rearward end of the barrel 130. The lip is adapted to seat against a flange or beaded rim that may be formed on the forward end of the vial assembly housing 152 so that the vial assembly can not be easily pulled out of the rear of the barrel 130. As a result, access to the retracted elements, and the contaminated needle in particular, is limited.

Referring now to FIGS. 20-22, the automatic retraction of the needle 112 shall be described. The vial assembly 150 is axially advanced to the proximal end of the barrel 130 until the medication 199 is completely expelled from the transfer chamber 155. As the vial assembly 150 is advanced, the forward rim of the housing 152 is displaced into engagement with the retaining arms 122 of needle retainer 120.

After the rim of vial assembly housing 152 engages the retaining arms 122, continued axial advancement of the vial assembly deflects the retaining arms radially inwardly so that the retaining tabs 124 are displaced inwardly, as shown in FIG. 20. In the inward position, the retaining tabs 124 are disengaged from the retaining apertures 138 of the barrel 130. In this way, the vial assembly 150 operates as an actuator, such that axial advancement of the vial assembly displaces the needle retainer 120 into an unlocked position. In the unlocked position, the needle retainer 120 is no longer locked in place against the force of the spring 126. After the needle retainer 120 is in the unlocked position and the user releases pressure on the vial assembly 150, the spring 126 propels the needle 112 rearwardly until the sharpened distal tip of the needle is enclosed within the barrel 130.

Locking Clip

Preferably, the needle assembly 115 includes a locking mechanism for preventing the rearward end of the needle from piercing the forward seal 156 before the medicine is drawn out of the vial 190 into the transfer chamber 155. As shown in FIGS. 9-12, the barrel 130 includes a locking clip 145 in the barrel wall to prevent the forward seal from being prematurely pierced. The wall of the barrel 130 includes a pair of radial slots 134 cut through a plane that is transverse to the longitudinal axis of the barrel. When the locking clip 145 is inserted through the slots 134, the clip prevents inadvertent forward displacement of the vial assembly 150 relative to the front seal 156, thereby preventing accidental advancement of the medicinal components through the needle 112. The locking clip 145 is preferably formed of a resilient high strength and high modulus resin, such as acetyl or polycarbonate, and is configured to releasably engage the slots 134 in the barrel 130.

Referring to FIG. 10, the locking clip 145 is preferably a flat member having a pair of resiliently deflectable legs 147 that join to form a U-shape. The open end of the locking clip 145 has tapered edges that allow the legs 147 to deflect outwardly as the locking clip is inserted into the sidewall of the barrel 130. In addition, the locking clip 145 has a plurality of teeth on the inside edge of the legs 147 that are adapted to engage the edges of the radial slots 134.

As the locking clip is inserted into the sidewall of the barrel 130, the legs 147 deflect outwardly to allow the teeth to clear the edges of radial slots 134. Upon being deflected outwardly, the resilience of legs 147 bias the legs radially inward toward their original position. Once the teeth are disposed within the slots 134, the legs 147 deflect radially inwardly toward their original position and releasably engage the outer edges of the needle retainer 120 in barrel 130. In the inserted position, the closed end of the locking clip 145 remains outside the barrel 130, as shown in FIGS. 9 and 11.

After the medicine is transferred from the vial 90 into the transfer chamber 155, the locking clip 145 is removed to permit the transfer chamber to be vented and the medicine 199 to be injected into the patient, as shown in FIGS. 14 and 15. The locking clip 145 is removed from the barrel 130 by pulling the closed end of the clip in a direction transverse to the longitudinal axis of the barrel. By pulling the clip in this manner, the legs are deflected outwardly from the slots 134 to allow the teeth to clear the edges of slots 134.

After the locking clip 145 is removed from the barrel 130, the medication 199 is injected into the patient by advancing the vial assembly forwardly into the barrel. Initially, the rearward needle pierces the forward seal. Then any air in the transfer chamber can be vented prior to injection. The needle 112 is the inserted into the patient, and continued forward displacement of the vial assembly 150 injects the medicine 199 into the patient.

Vial Assembly

Referring to FIG. 11, the details of the vial assembly will be described in detail. The vial assembly 150 comprises an elongated hollow housing 152 having a fluid chamber referred to as the transfer chamber. A vial holder 180 is attached to the rearward end of the housing 152. The vial holder 180 retains the vial 190 of medicine. A valve 170 attached to the vial holder 180 controls the flow of fluid from the vial into the transfer chamber 155. A spring housing 155 houses a torsion spring 156 that biases the valve toward a closed position.

The vial assembly housing 152 is an elongated generally cylindrical hollow element. A pair of elongated ribs 154 formed on the outer surface of the housing 152 cooperate with a pair of grooves formed in the interior of the barrel to prevent the housing from twisting relative to the barrel, as shown in FIGS. 9, 17 and 19. The forward end of the housing is sealed by a forward seal 156 that cooperate with a barbed connector on the needle hub 121 to attach the vial assembly 150 to the needle assembly 115. The forward seal 156 forms the forward end of the transfer chamber.

Front Seal

The front seal 156 is an elastomeric seal, which may be molded in a self-sealing biocompatible elastomer such as polyisoprene. The front seal 156 is generally cylindrical, having a plurality of axially-spaced circumferential ribs 181. The ribs 181, which are more clearly shown in FIG. 10, frictionally and sealingly engage the interior of the container to provide a fluid tight seal, thereby preventing fluid from leaking from the vial 150. The front seal 156 also has a front end that is pierceable by the rearward sharpened tip of needle 112. After being pierced, the front end of the front seal 156 reseals around the needle 112 to prevent fluid from leaking from the vial 150.

The front seal 156 includes an elongated reduced diameter neck. A substantially cylindrical sleeve 140 surrounds the neck portion of the front seal, as shown in FIG. 12. The sleeve 140 comprises a slot through the length of the sleeve.

Referring now to FIGS. 13 and 14, the front seal 156 has a socket 157 configured to cooperate with the barbed connector 125 on the needle hub 121. The socket 157 includes two radially relieved recesses that mate with the barbed connector 125. Specifically, the barbed connector 125 matingly engages the front seal 156 in a first position and a second position.

In the first position, the barbed connector 125 engages the first recess, as shown in FIG. 12. In this position, the vial is attached to the hub, but the rearward end of the needle does not pierce the front seal 156. Displacing the vial assembly forwardly relative to the hub, displaces the forward seal over the barb into the second position. In the second position, the barbed connector 125 engages the second recess, as shown in FIG. 15. In this position, the rearward end of the needle 112 pierces the front seal 156.

The front seal 156 includes an elongated hollowed bore in which the rearward end of the needle projects. The rearward end of the bore is sealed by a pierceable wall. As shown in FIG. 12 prior to use, the vial 150 is mounted in the first position so that the barbed connector 125 engages the first recess. In this position, the needle 112 does not penetrate the pierceable wall in the forward seal. As the vial assembly is displaced forwardly, hub 121 engages the second recess in the forward seal, and the rearward end of the needle 112 pierces the wall so that the needle is in fluid communication with the transfer cavity. After the needle 112 penetrates the pierceable wall, the wall reseals around the needle to form a fluid-tight seal and prevent medication in the vial assembly 150 from leaking around the needle.

The connection between the front seal 156 and the needle hub 121 is preferably a one-way engagement. In other words, when the front seal 156 is mounted on the barbed connector 125, the vial assembly 150 can be displaced forwardly relative to the barbed connector, but the vial assembly cannot be displaced rearwardly relative to the barbed connector. In this way, the vial assembly 150 cannot be readily removed from the needle hub 121 in the barrel 130, such that the vial assembly is substantially permanently attached to the needle hub and barrel.

The one-way connection is facilitated by the rearward-facing tapered shoulder of the barbed connector 125 and the square shaped forward-facing shoulder of the recesses in the forward seal 156. In particular, the rearward-facing shoulder of the barbed connector 125 cooperates with tapered sides in the first and second radial recesses to permit relative displacement of the plug from the first recess to the second recess. Reverse displacement from the second recess back to the first recess is resisted by the square shaped forward-facing shoulders on barbed connector 125, which act to impede reverse displacement.

Referring now to FIG. 12, the front seal 156 is configured to prevent ejection of fluid when the barbed connector 125 is displaced from the first position, in which the barbed connector 125 engages the first radial recess, to the second position, in which the barbed connector engages the second radial recess. Specifically, the front seal 156 includes a flared head or circumferential flange at the forward end of the front seal. The open forward end of the sleeve 140 surrounding the forward seal may be formed with a beaded rim that seats against the rearward edge of the flared head. The outside diameter of the flared head is greater than the inside diameter of the sleeve 140, thereby impeding rearward displacement of the front seal 156 into the vial assembly is displaced forward after the locking clip 145 is removed. In addition, the force required to overcome the frictional engagement between the outer circumference of the front seal 156 and the inner wall of the vial 150 is greater than the force required to displace the plug 125 from the first recess to the second recess. Accordingly, when force is initially applied to the vial assembly 150, the front seal 156 remains in a fixed position relative to the vial 150, while the barbed connector 125 is displaced into the second position. This restriction on the front seal 156 limits the release of fluid from the vial 150 when the needle 112 pierces the wall in the forward seal.

The rearward end of the vial assembly housing 152 is sealed by a rearward seal 160 that forms a fluid-tight seal with the interior of the housing. The rearward seal forms the rearward end of the transfer chamber. As shown in FIGS. 17 and 19 the rearward seal 160 comprises an internal bore forming a fluid tight seal with the valve 170. In addition, the rearward seal 160 includes an axial channel or recess 162 intersecting the bore, forming a fluid passage allowing fluid to flow from the vial 190 into the transfer chamber when the valve is open.

Referring to FIGS. 12, 13, 16 and 18, the spring housing 165 is integrally formed on the rearward end of the housing 152. The spring housing flares out radially from the housing forming an annular space having a greater diameter than the housing. The spring housing comprises a channel forming a guide slot 167 that cooperates with a stop pin 169 to limit the rotation of the valve as discussed further below. A torsion spring in the spring housing bears against the stop pin 169 and a post 168 to bias the valve into the closed position. In addition, the spring housing forms a pair of radially extending surfaces forming finger grips for use in attaching the vial 190 to the vial assembly 150, as discussed further below.

The vial holder 180 is pivotably displaceable within the spring housing 165. The vial holder comprises a socket for receiving the vial 190. A pair of radially deformable arms 185 lock the vial into the vial holder. A piercing element 182 projects into the vial holder socket and is operable to pierce the vial 190. The vial holder 180 forms a cap for the spring housing. A plurality of latches formed on the spring housing 165 attach the vial holder 180 to the spring housing.

The valve 170 is integrally formed with the vial holder 180. The valve projects forwardly from the vial holder and into engagement with the rearward seal 160. As shown in FIG. 12, preferably the valve 170 comprises an external barb for substantially permanently attaching the valve to the seal. A valve comprises a central bore having a closed forward end adjacent the rearward seal. The piercing element is fixed attached to the valve within the central bore of the valve, so that the valve is in fluid communication with the piercing element. A side port in the valve selectively engages the channel 162 through the rearward seal as discussed further below.

Referring again to FIGS. 10 and 12, the vial 190 is a generally cylindrical bottle that may be molded out of pharmaceutical quality glass such as borosilicate, or a rigid inert plastic such as polyolefin or polyester. The bottom of the vial is integral with the sides, so that it is fixed relative to the sidewalls. The forward end of the vial is sealed by a resealable pierceable elastomeric septum 195. The septum 195 is fixed relative to the glass vial by an annular cap 197 that is crimped around a circumferential flange formed on the forward end of the vial.

The vial 190 contains a pre-filled dose of medication. The medication is drawn out of the vial and injected into the patient as discussed further below. Alternatively, the vial assembly can be configured to accommodate a multi-dose vial in which a dose of medication is drawn out of the vial and injected to the patient. After the injection, the needle is retracted. The vial can be removed from the device 110 and the device is safely disposed in a sharps container. The vial can then be used with a new device for a subsequent injection. The locking arms 185 preferably engage the flared head of the vial to substantially permanently attach the vial to the vial holder. Alternatively, if the device is used in connection with a multiple dose vial, the arms are configured to releasably lock the vial to the vial injector.

Use of Device

Referring now to FIGS. 12-22, the operation of the injection device 110 will be described. Prior to use, the needle 112 is disposed in an extended position so that the distal end of the needle projects forwardly from the barrel 130, as shown in FIG. 12. Preferably, the device 110 is shipped with the vial assembly 150 already mounted in barrel 130 so that the barbed connector 125 is engaged in the first recess in the forward seal 156. Alternatively, the vial assembly 150 may be shipped separately from the barrel 130, so that the vial must be attached to the barrel prior to use.

As shown in FIG. 12, prior to use, the vial assembly housing 152 is partially withdrawn so that the transfer chamber 155 is an empty space containing air. The vial 190 is inserted into the vial holder 180 so that the piercing element pierces the septum 195 on the vial. The operator may grasp the spring housing with his or her fingers and urge the vial forward with his or her thumb to insert the vial into the vial holder without urging the vial assembly 150 forwardly.

The vial 180 is then pressurized as follows. The device 110 is held vertically upright as shown in FIG. 12. The vial holder 180 is rotated approximately 90 degrees as shown in FIGS. 17 and 19 to open the valve 170. When holding the valve open, the housing 152 is urged forwardly over the forward seal 156. The housing is displaced forwardly until it abuts the locking clip 145. This is illustrated in FIG. 13, except that in FIG. 13, the housing has yet engaged the locking clip. In this way, the air in the transfer chamber 155 is forced into the vial 190 to pressurize the contents of the vial.

After vial 190 is pressurized, the device 110 is inverted so that the vial is vertically oriented above the transfer chamber 155, as shown in FIG. 14. The housing 152 is then displaced rearward over the forward seal while the valve is maintained in the open position. This creates a vacuum in the transfer chamber, which draws the medicine 99 out of the vial and into the transfer chamber as shown in FIG. 14.

In the figures, the housing is elongated so that the forward seal 156 is spaced rearwardly from the rearward seal after the vial is pressurized, as shown in FIG. 13. However, it may be desirable to shorten the housing 152 so that the forward seal abuts the rearward seal after pressurization. This will tend to increase the vacuum created when the housing is subsequent pulled rearwardly to draw the medicine 199 out of the vial.

Once the medicine is drawn into the transfer chamber 155, the medicine should be vented prior to injection to ensure that air is not injected into the patient. Accordingly, the device is inverted again, so that the needle is disposed vertically above the transfer chamber 155, as shown in FIG. 15. The locking clip 145 is then removed so that the vial assembly 150 can be displaced forwardly so that the rearward end of the needle pierces the forward seal. The housing is the advanced over the forward seal to vent the air from the transfer chamber 155. Subsequently, the forward tip of the needle 112 is inserted into the patient and the vial assembly 150 is driven forwardly to inject the medicine into the patient from the transfer chamber 155.

At the end of the injection stroke, the rim on the vial assembly housing 152 engages the retaining arms 122, thereby displacing the retaining tabs 124 radially inwardly to disengage the needle retainer 120 into the unlocked position. Although the needle retainer 122 is in the unlocked position, the needle 112 does not retract until the user releases pressure from the vial assembly. In this way, the user can retain pressure on the vial assembly until after the needle is withdrawn from the patient. The user can then release pressure from the vial assembly so that the needle is propelled rearwardly by the spring 126. Alternatively, the user can release pressure from the vial assembly while the needle 112 is still inserted in the patient. Once the vial assembly is released, the spring 126 propels the needle 112 rearwardly so that the contaminated distal tip of the needle is enclosed within the barrel 130.

Referring now to FIGS. 23-30, a second alternate embodiment of a vial injector for injecting fluid from a pre-filled vial is designated 210. The device 210 includes an injection needle 239 having a sharpened tip for piercing a patient. After injection, the injection needle 239 is automatically shielded to prevent inadvertent contact with the contaminated needle.

The device 210 comprises an injector assembly 215 and a vial holder assembly 240. The vial holder 240 holds a vial 270 of medicine, and is attached to the injector assembly 215. The injector assembly 215 has a barrel 220 for receiving the vial holder 240, and a needle hub 235 that carries the injection needle 239.

Figure 23:
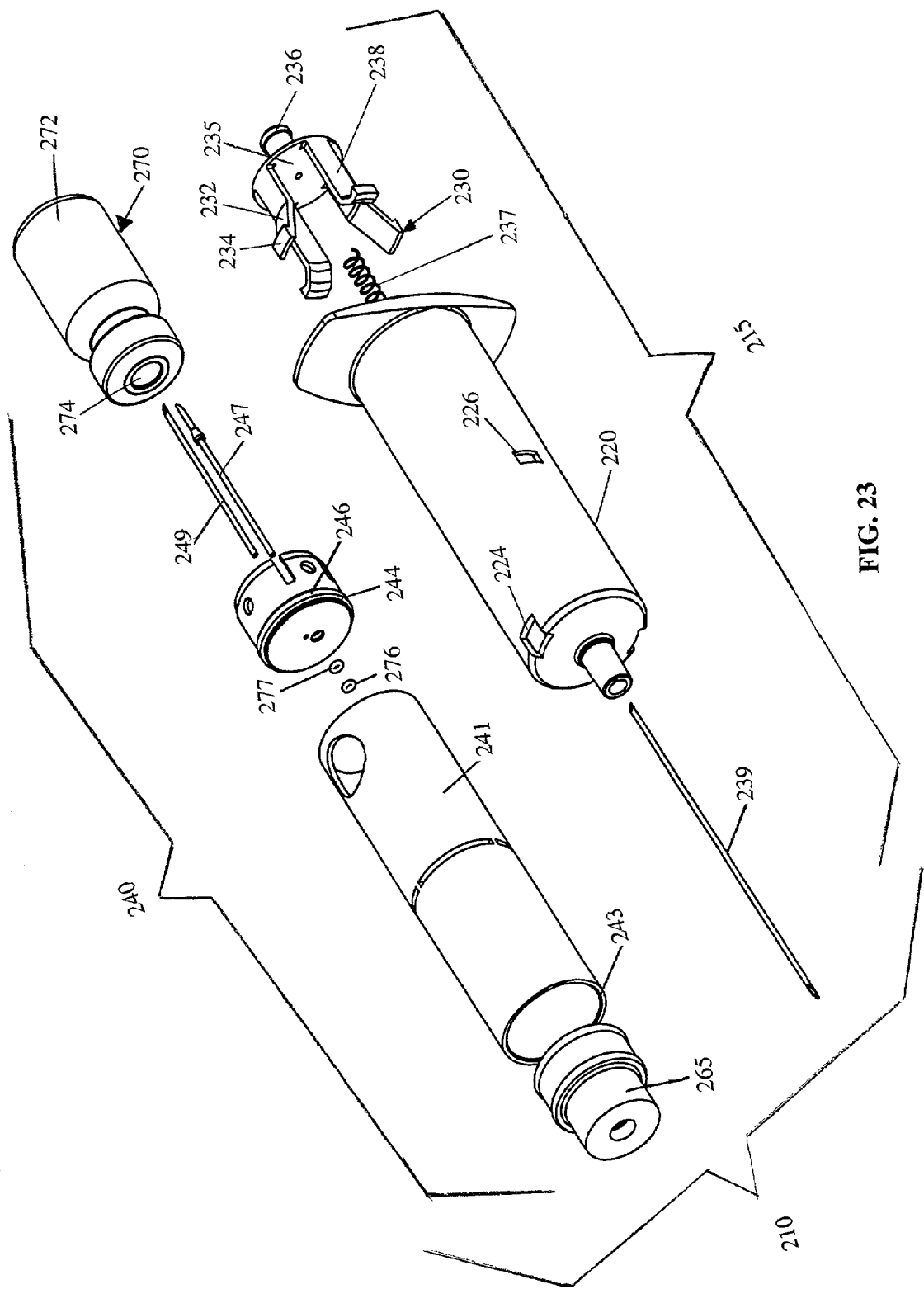
FIG. 23 is an exploded perspective view of an second alternative embodiment of a safety prefilled vial injection device.

Referring to FIGS. 23, 28 and 30, the injection needle 239 is a double-ended needle that is operable between two positions, an extended position and a retracted position. In the extended position, the injection needle 239 projects forwardly from the forward end of the barrel 220. In the retracted position, the injection needle is retracted into the barrel so that the forward sharpened tip of the needle is enclosed within the barrel to prevent inadvertent contact with the sharpened tip. When the injection needle 39 is in the extended position, a spring 237 biases the needle rearwardly toward the retracted position. A needle retainer 230 releasably retains the injection needle in the extended position against the bias of the spring. During the injection stroke, the vial holder 240 cooperates with the needle retainer 230 to allow the injection needle to retract into the barrel 220, as shown in FIG. 29.

Some pre-filled injectors utilize a pre-filled cartridge or ampule having a seal or plug that is displaceable to eject medicine from the cartridge or ampule. The present device may be utilized with such cartridges and/or ampules. However, preferably, the present device utilizes a pre-filled vial 270 formed of a container 272 that has fixed walls and a seal 274 that is not displaceable. During use, the medicine is withdrawn from the vial and then expelled.

Figure 24:
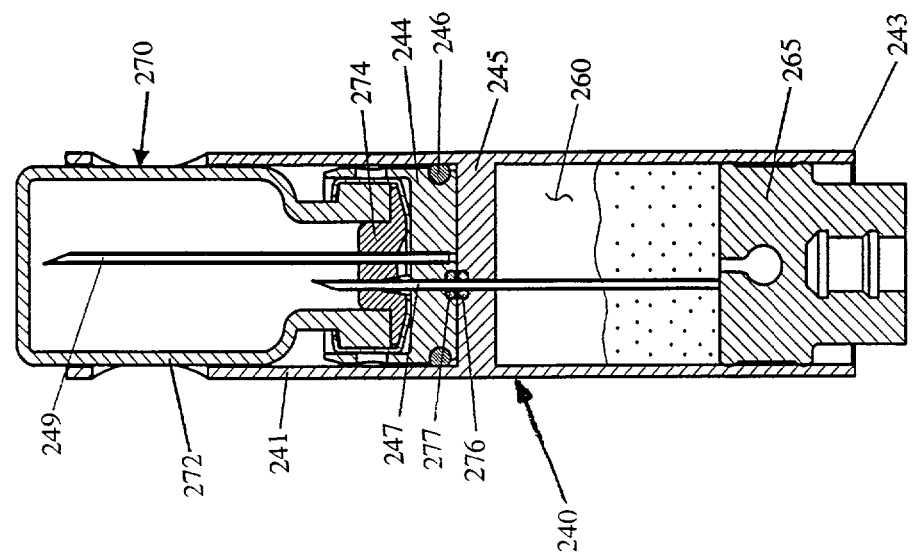
FIG. 24 is an enlarged cross-sectional view of a vial assembly of the device illustrated in FIG. 23.

For instance, referring to FIG. 24, the device 210 comprises a vial holder assembly 240, which has an empty transfer chamber 260 for receiving medicine from the vial. During use, the medicine is transferred out of the vial 270 under positive pressure into the transfer chamber. The medicine is then ejected from the transfer chamber 260 into the patient.

Figure 25:
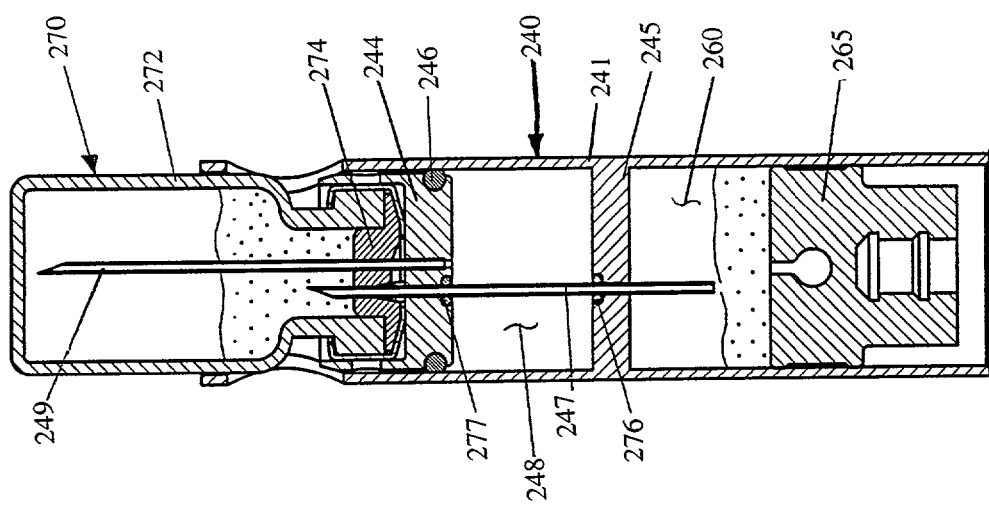
FIG. 25 is a cross-sectional view of the vial assembly illustrated in FIG. 24, illustrating the vial assembly during transfer of fluid.
Figure 26:
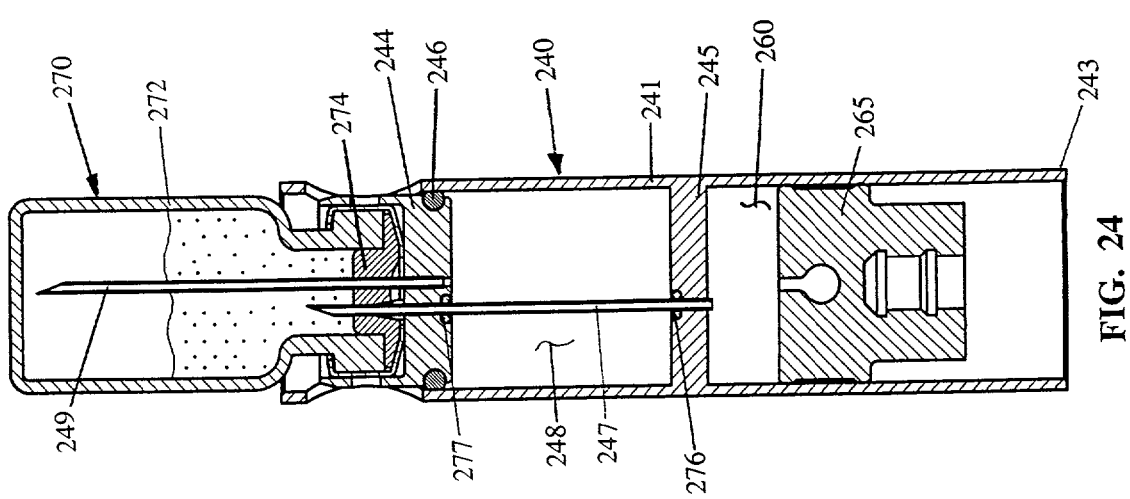
FIG. 26 is a cross-sectional view of the vial assembly illustrated in FIG. 24, illustrating the vial assembly after completion of fluid transfer.

More specifically, referring to FIGS. 24-26, the medicine from the vial is transferred out of the vial 270 by pushing the vial 270 forwardly to pressurize the fluid in the vial. The pressurized fluid is then transferred into the transfer chamber 260. Any air that is present in the transfer chamber 260 can then be vented. The medicine can then be injected into the patient by driving the vial holder 240 forwardly.

To inject the medicine, the vial 270 and vial holder 240 are driven forwardly to expel the medicine from the transfer chamber 260. At the end of the injection, the forward end of the vial assembly 240 engages the needle retainer 230 thereby releasing the needle 239 for retraction, as shown in FIG. 29. The spring 237 then displaces the needle rearwardly so that the contaminated needle is shielded within the barrel 220, as shown in FIGS. 30.

Injector Assembly

The details of the injector assembly 215 are substantially similar to the injector assembly 15 of the first embodiment described above and illustrated in FIGS. 1-8. Specifically, the injector assembly 215 comprises a barrel 220 and a needle retainer 230 releasably retaining the injection needle 239. A needle hub 235 attached to the needle retainer 230 has a mounting stem 36 for attaching the vial holder 240 to the injector assembly 215.

The needle retainer 230 is attached to the needle hub 235, and preferably is integrally molded with the needle hub as a single piece. Prior to retraction, the needle retainer 230 maintains the needle hub 235 and attached needle 239 in a fixed axial position while the medication is expelled from the vial holder 240. After the injection, the needle retainer 230 releases the needle hub 235 and the attached needle 239 is displaced rearwardly by a compression spring 237.

Referring again to FIGS. 23 and 28, the needle retainer 230 includes a pair of retaining arms 232 that extend radially outwardly and forwardly from the distal end of the needle hub 235. During operation, the needle retainer 230 is operable between a locked position and an unlocked position. In the locked position, the retaining arms 232 engage the retaining apertures 224 in the barrel wall to maintain the needle in a fixed axial position with the forward tip of the injection needle 239 projecting forwardly from the barrel 220. More specifically, in the locked position, the retaining arms 232 engage the barrel 220 to hold the needle hub 235 and needle 239 against the rearward bias of the spring 237. In the unlocked position, the retaining arms 232 are positioned so as to allow the needle hub 235 and needle 239 to be retracted rearwardly, as shown in FIG. 29. More specifically, in the unlocked position, the retaining arms 232 are disengaged from the retaining apertures 224, allowing the spring 237 to propel the needle hub 235 and needle 239 rearwardly as shown in FIG. 30.

Referring to FIG. 28, as discussed above, the retaining arms 232 on the needle retainer 230 project forwardly and outwardly into engagement with the retaining apertures 224 in the wall of the barrel 220. The terminal end of each arm forms a retaining tab 234 that is configured to project into a retaining aperture 224. More specifically, the retaining tabs 234 engage the lip formed by each retaining aperture 224 in the wall of the barrel 220. In this way, the retaining tabs 234 operate as a pair of latches to retain the needle hub 235 and the injection needle 239 against the rearward bias of the spring.

As shown in FIG. 30, when the injection needle 239 is retracted, the needle, needle retainer 230 and vial holder 240 are displaced rearwardly together. Preferably, the injection device 210 includes a mechanism for limiting rearward displacement of the retracted elements. Specifically, as shown in FIG. 30, the injector assembly 215 preferably includes a pair of guide arms 238 that cooperate with a pair of lockout windows 226 in the barrel 220 to lock the retracted elements in the retracted position after use. The guide arms 238 cooperate with a pair of alignment channels or grooves formed in the interior wall of the barrel 220. The guide arms 238 extend forwardly from the needle hub 235 and project radially outwardly into engagement with the alignment grooves.

The lockout windows 226 are adapted to receive the forward ends of the guide arms 238, as shown in FIG. 30. In particular, as the front end of each guide arm 238 aligns with the corresponding lockout window 226 during needle retraction, the radially outward bias of the guide arm displaces the arm outwardly so that the forward end projects into the lockout window. The engagement between the guide arms 238 and lockout windows 226 prevent further axial movement of the injection needle 239. As a result, the retracted elements are limited from further displacement in the forward or rearward direction.

Referring now to FIGS. 28-30, the automatic retraction of the injection needle 239 shall be described briefly. The vial holder 240 is axially advanced to the proximal end of the barrel 220 until the medication is completely expelled from the transfer chamber 260 as shown in FIGS. 28 and 29. As the vial holder 240 is advanced, the forward rim 243 of the housing 241 is displaced into engagement with the retaining arms 232 of needle retainer 230.

After the rim 243 of the vial holder housing 241 engages the retaining arms 232, continued axial advancement of the vial holder deflects the retaining arms radially inwardly so that the retaining tabs 234 are displaced inwardly, as shown in FIG. 29. In the inward position, the retaining tabs 234 are disengaged from the retaining apertures 224 of the barrel 220. In this way, the vial holder 240 operates as an actuator, such that axial advancement of the vial holder assembly displaces the needle retainer 230 into an unlocked position. In the unlocked position, the needle retainer 230 is no longer locked in place against the force of the spring 237. After the needle retainer 230 is in the unlocked position and the user releases pressure on the vial holder 240, the spring 237 propels the needle 239 rearwardly until the sharpened distal tip of the needle is enclosed within the barrel 220.

Vial Holder Assembly

Referring to FIGS. 23-26, the details of the vial holder assembly 240 will be described in detail. The vial holder 240 comprises an elongated hollow housing 241 that is divided into two chambers by a mid-wall 245. The forward chamber is a transfer chamber 260, the rearward chamber is an air-pump chamber 248. A forward seal 265 seals the front of the transfer chamber 260 and a slidable vial carrier 244 seals the rearward end of the air-pump chamber 248.

The needle carrier 244 includes two needles. The first needle is a pressurizing needle 249 in fluid communication with the air-pump chamber 248 and the vial 270. The second needle is a transfer needle 247 in fluid communication with the transfer chamber 60 and the vial 270.

The rearward end of the transfer needle 247 projects into the socket in the vial carrier 244 to pierce the septum 272 on the vial. Preferably, the length of the transfer needle projecting into the carrier socket is slightly longer than the thickness of the vial septum. In this way, the heel of the needle bevel is spaced from the inner edge of the septum a short distance which preferably is less than the length of the needle bevel.

The transfer needle 247 extends through a hole in the needle carrier 244 and through a hole in the mid-wall 245, so that the rearward sharpened tip projects rearwardly into the needle carrier socket and the forward end projects into the transfer chamber 260. In this way, the transfer needle spans from the vial 270 to the transfer chamber 260. The transfer needle 247 is slidable relative to the mid-wall 245 and the needle carrier 244. Accordingly, preferably a mid-wall seal 276 forms a fluid tight seal between the transfer needle 247 and the mid-wall 245, and a carrier seal 277 forms a fluid tight seal between the transfer needle and the vial carrier 244. As shown in FIG. 23, preferably the seals 276, 277 are o-ring seals. However, other types of seals can be employed to provide a fluid-tight sliding fit between the transfer needle and the needle carrier and mid-wall.

The pressurizing needle 249 preferably projects into the socket of the vial carrier 244 further than the transfer needle 247, so that the pressurizing needle 249 is adapted to project further into the vial 270, as shown in FIG. 24. In this way, preferably when the vial 270 is mounted in the vial holder assembly 240 and held upright, the pressurizing needle 249 projects into the vial adjacent the bottom of the vial to pressurize the air in the vial.

As mentioned previously, the front seal 265 seals the forward end of the transfer chamber 260. The front seal 265 cooperates with the barbed connector 236 on the needle hub 235 to attach the vial holder assembly 240 to the injector assembly 215. The front seal 265 is substantially similar to the front seal 265 in the first device 110, and the details of the front seal are provided previously in the description of the first device. The front seal 265 has a wall that is pierceable by the rearward sharpened tip of the injection needle 239. After being pierced, the front end of the front seal 265 reseals around the needle 239 to prevent fluid from leaking from the transfer chamber 260.

Referring to FIG. 24, the rearward end of the vial holder housing 241 is sealed by the vial carrier 244. The vial carrier is a cylindrical element, having a circumferential groove around its exterior, into which a carrier seal 246 is seated. The carrier seal 246 is an elastomeric seal, such as an o-ring, that forms a fluid-tight seal between the vial carrier 244 and the interior wall of the vial holder housing 241. In addition, the carrier seal 246 provides a sliding seal so that the vial carrier 244 can slide within the housing 241, while maintaining an air-tight seal with the interior wall of the housing. This sliding seal allows the vial carrier 244 to operate as a piston to pump air into the vial 270 as described further below.

The rearward end of the vial carrier 244 is open, forming a socket configured to cooperate with and receive a vial. Specifically, the socket is adapted to receive the head of a vial, as shown in FIG. 24, so that preferably there is a light interference fit between the head of the vial and the interior of the socket. In this way, the vial carrier 244 grips the vial to secure the vial in the vial carrier. As in the first embodiment described previously, the vial carrier 244 may cooperate with an annular ridge formed in the interior of the housing 241 to prevent axial displacement of the carrier 244 when the vial 270 is inserted into the carrier. However, in the present instance, the housing does not include such a ridge.

Method of Operation

Before describing the details of operation, a short summary is provided. First, the vial 270 is inserted into the vial holder 240 so that the transfer needle 247 and the pressurizing needle 249 pierce the septum 274 on the vial (see FIG. 24). The vial 270 and vial carrier 244 are displaced forwardly to pump air into the vial 270 from the air pump chamber 248 to pressurize the vial (see FIG. 25). The pressurized medicine in the vial then flows into the transfer chamber 260 (see FIG. 26). The rearward end of the injection needle 239 pierces the front seal 265 (see FIG. 27), and air is purged from the transfer chamber 260. The medicine is then injected into the patient by driving the vial holder 240 forwardly (see FIGS. 28 and 29). At the end of the injection stroke, the forward rim 243 of the vial holder assembly 240 engages the needle retainer 230, displacing the needle retainer arms 232 inwardly (see FIG. 29). The spring 237 then displaces the needle hub 235 and needle 239 rearwardly, along with the vial holder assembly 240 (see FIG. 30). At the end of retraction, the locking arms 238 engage the lockout windows 226 to lock the needle in the retracted position. The shielded device 210 can then be disposed of safely.

The operation of the device 210 will now be described in detail. Prior to use, the air pump chamber 248 and the transfer chamber 260 are empty. Referring to FIG. 24, the vial 270 is inserted into the rearward end of the vial holder 240 so that the head of the vial seats in the vial carrier 244 and the rearward end of the transfer needle 247 and pressurizing needle 249 pierce the septum 274 on the vial.

After the transfer needle 247 pierces the septum 274, the vial 270 is displaced forwardly, which in turn displaces the vial carrier 244 forwardly into the air-pump chamber 248. Since the carrier seal 246 forms a fluid-tight seal with the interior of the housing, displacing the carrier 244 forwardly pumps the air from the air pump chamber 248 into the vial 270, which pressurizes the vial and transfers medicine into the transfer chamber 260 from the vial 270, as shown in FIG. 25. The vial is preferably held upright as shown in FIG. 25 so that gravity aids in the flow of fluid from the vial to the transfer chamber 260.

As the vial carrier 244 is displaced forwardly, the transfer needle 247 slides forwardly relative to the mid-wall 245. In addition, the front seal 265 displaces forwardly to increase the volume of the transfer chamber as the pressurized medicine is transferred to the transfer chamber. At the end of the transfer stroke, the forward tip of the transfer needle 247 engages the front seal 265 so that the front seal seals the transfer needle to prevent medicine from leaking from the transfer chamber 260 back into the vial 270.

As shown in FIGS. 24-26, the medicine can be transferred to the transfer chamber 260 before attaching the vial holder assembly 240 to the needle assembly 215. However, if desired, the vial holder assembly 240 can be attached to the needle assembly 215 before transferring the medicine into the transfer chamber. Accordingly, if the vial holder assembly is not yet attached to the needle assembly, it is attached after the medicine is transferred.

After the medicine is transferred and the vial holder 240 is attached to the injection assembly 215, the device is flipped vertically so that the injection needle 239 is directed upwardly, as shown in FIG. 27. The vial holder assembly 240 is then displaced forwardly into the barrel 220 so that the front seal moves forwardly, and the barbed connector pops into the second recess in the front seal 265. In doing so, the rearward tip of the injection needle 239 pierces the front seal 265 so that the injection needle is in fluid communication with the transfer chamber 260. Once the barbed connector 236 engages the second socket in the front seal 265, the needle hub maintains the front seal at a fixed axial position as the vial holder 240 is displaced forwardly.

Any air in the transfer chamber is purged by displacing the vial holder 240 forwardly over the front seal while holding the device 210 with the needle upwardly. After the air is purged, the device is ready to inject, as shown in FIG. 28. The forward sharpened tip of the injection needle 239 may then be inserted into the patient, and the medicine is injected into the patient by driving the vial holder housing 241 forwardly.

Displacing the vial holder assembly 240 forwardly relative to the injection assembly 215 drives the housing 241 over the axially fixed front seal 265, thereby expelling the medicine from the transfer chamber. At the same time, the mid-wall 245 and vial carrier 244 slide relative to the transfer needle 247, as shown in FIGS. 28 and 29. At the end of the injection stroke, the forward rim of the housing 241 engages the arms 232 of the needle retainer 230, displacing the arms radially inwardly, as shown in FIG. 29. At this point, the injection needle 239 is released for retraction. As soon as the operator releases pressure against the rearward end of the vial holder assembly 240, the spring 237 displaces the needle hub 235 and attached needle rearwardly, along with the vial holder assembly.

As the injection needle 239 is retracted, the guide arms 238 ride in the guide slots in the interior of the barrel, until the ends of the guide arms reach the lockout windows 226. At this point, the guide arms resiliently displace outwardly into the lockout windows 226, thereby locking the needle hub 235 and attached needle 239 in the retracted position. In this way, the sharpened tip of the contaminated needle is automatically protected against inadvertent contact after use, and can be safely disposed of, preferably in a sharps container.

The terms and expressions which have been employed are used as terms of description and not of limitation. There is no intention in use of such terms and expressions of excluding any equivalents of the features shown and described or portions thereof. It is recognized, however, that various modifications of the embodiments described herein are possible within the scope and spirit of the invention. For instance, the different embodiments have been described as safety devices in which the needle is automatically shielded after use. However, in certain applications, the present invention may be employed without the safety feature. Specifically, the device may be modified to incorporate the automatic withdrawal and injection of the medication from the vial without the safety features. In addition, it is possible to modify the present invention by eliminating the pressurization of the vial and rely on gravity or some other means to transfer the medication from the vial. Furthermore, other changes to the structure can be made, such as in the second embodiment 110, the torsion spring may be eliminated, and a pair of detents can be used to releasably lock the valve in the open and closed positions. Further still, the device can be modified to include a step in which two separate components are mixed prior to injection. Specifically, in the foregoing description, the device includes a transfer chamber for receiving the medicinal fluid from the vial. The transfer chamber has been described as an empty chamber. However, it may be desirable to store a component, such as a powder, in the sealed transfer chamber. Then, prior to injection, the fluid from the vial is transferred into the transfer chamber and mixed with the powder. The mixture can then be injected into a patient. Furthermore, in the description above the devices are described as incorporating a transfer chamber for receiving medicinal fluid from the vial. In certain instances the device need not have such a transfer chamber. Accordingly, the present invention incorporates modifications and variations that fall within the scope of the following claims.

The invention claimed is:

1. A medical device for injecting medicinal fluid from a vial having a container and an amount of medicinal fluid, comprising:
   a hollow barrel;
   a vial holder displaceable within the barrel having a socket configured to receive the vial;
   an air-pump chamber within the barrel configured to pump air into the vial;
   a needle having a sharpened tip operable between an exposed position in which the sharpened tip projects forwardly from the barrel and a shielded position in which the sharpened tip is shielded from contact;
   a transfer chamber within the barrel for receiving the medicinal fluid from the vial, wherein the transfer chamber is adapted to be in fluid communication with the needle;
   a transfer seal disposed within the barrel between the transfer chamber and the air-pump chamber; and
   wherein after use, the needle is disposed in the shielded position.

2. The metal device of claim 1 wherein the transfer seal comprises a transfer conduit configured to extend between the vial and the transfer chamber for transferring medicine from the vial to the transfer chamber.

3. The medical device of claim 1 wherein the vial holder Is at least partially disposed within the barrel.

4. The device of claim 1 comprising a piston operable to pump air from the air-pump chamber Into the vial to pressurize the fluid In the vial.

5. The device of claim 1 comprising a lock releasably locking the vial holder and the barrel to prevent relative motion between the vial holder and the barrel.

6. The medical device of claim 1 comprising a piston for expelling medicine out of the transfer chamber through the needle.

7. The medical device of claim 1 wherein the transfer chamber is displaceable relative to the needle.

8. The medical device of claim 1 comprising a valve adapted to control the flow of fluid between the transfer chamber and the vial.

9. The medical device of claim 8 wherein the valve is a sliding valve.

10. The medical device of claim 1 comprising a pierceable rear seal adapted to provide a fluid-tight seal between the vial and the transfer chamber.

11. The device of claim 1 comprising a pierceable forward seal providing a fluid-tight seal between the transfer chamber and the needle.

12. The device of claim 1 comprising a biasing element biasing the needle toward the shielded position.

13. The device of claim 12 comprising a needle retainer releasably retaining the needle in the exposed position against the bias of the biasing element.

14. The device of claim 13 wherein the needle retainer is configured so that the needle is automatically released for retraction at the end of an injection.

15. A medical device, comprising:
   a vial containing a quantity of medicinal fluid, wherein the vial comprises a container having a fixed rearward wall closing the rearward end of the container and a fixed pierceable wall sealing the forward end;
   a holder configured to receive the vial;
   an air-pump chamber configured to pump air into the vial;
   an injection needle for expelling the medicinal fluid from the device wherein the injection needle comprises a sharpened tip operable between an extended position in which the sharpened tip is exposed for use and a protected position in which the sharpened tip is shielded to prevent inadvertent contact with the sharpened tip;
   a biasing element biasing the needle toward the retracted position;
   a needle retainer releasably retaining the needle in the extended position against the bias of the biasing element;
   a communication path adapted to establish fluid flow between the vial and the injection needle to allow the medicinal fluid to flow from the vial to the injection needle;

a transfer chamber disposed within the communication path for receiving the medicinal fluid from the vial, wherein the medicinal fluid is subsequently expelled from the transfer chamber through the injection needle;

a transfer seal disposed between the air-pump chamber and the transfer chamber, wherein the transfer seal defines a boundary of the air-pump chamber and wherein the transfer seal is pierceable to allow medicinal fluid transfer between the vial and the transfer chamber; and wherein after use the needle is disposed in the protected position.

16. The device of claim 15 comprising a conduit extending between the vial and the chamber.

17. The device of claim 15 wherein the chamber is disposed in a first housing.

18. The device of claim 17 comprising a pierceable seal sealing an end of the chamber.

19. The device of claim 17 wherein the device comprises a second housing associated with the injection needle, wherein the first housing is displaceable relative to the second housing.

20. The device of claim 19 comprising a stop for releasably impeding relative displacement between the first and second housings.

21. The device of claim 19 wherein displacing the first housing relative to the second housing operates to expel the medicinal fluid from the chamber through the injection needle.

22. The device of claim 19 comprising a valve controlling the flow of medicinal fluid from the chamber.

23. A medical device cooperable with a needle assembly having a retractable injection needle and a pre-filled container of medicinal fluid, the medical device comprising:

a housing cooperable with the needle assembly;

a socket for receiving the pre-filled container;

a pressurizing element external to the pre-filled container and within the housing to provide positive fluid pressure within the pre-filled container when the pre-filled container is disposed in the socket;

an empty chamber in the housing configured to receive medicinal fluid from the pre-filled container and to deliver medicinal fluid to the injection needle, wherein the chamber is configured to receive substantially all of the medicinal fluid from the pre-filled container prior to establishment of fluid communication between the chamber and the injection needle; and a transfer seal disposed between the chamber and the pressurizing element, the transfer seal comprising a conduit for providing a fluid path between the chamber and the pre-filled container when the pre-filled container is disposed in the socket;

wherein the housing has an activation surface cooperable with the needle assembly and configured to activate retraction of the needle after use.

24. The device of claim 23 comprising a pierceable seal sealing the chamber.

25. The device of claim 23 comprising a fluid path extending between the pre-filled container and the needle assembly when the needle assembly is attached to the housing and the pre-filled container is disposed in the socket.

26. The device of claim 25 comprising a valve controlling the flow of fluid along the fluid path.

27. The device of claim 17 wherein the valve is a sliding valve.

28. The device of claim 23 comprising a stop for releasably retaining the housing from displacement relative to the needle assembly when the needle assembly is connected with the housing.

29. A medical device for injecting medicinal fluid from a vial containing an amount of medicinal fluid, comprising:

a hollow barrel connectable with the vial;

a needle having a sharpened tip operable between an exposed position in which the sharpened tip projects forwardly from the barrel and a retracted position in which the sharpened tip is shielded from contact;

a biasing element biasing the needle rearwardly toward the retracted position;

a retainer releasably retaining the needle in the exposed position;

a holder engageable with the barrel, wherein a socket is formed in the holder for receiving the vial;

an air-pump chamber disposed within the holder, and a piston operable to pump air from the air-pump chamber into the vial to provide positive air pressure within the vial, wherein the holder is displaceable relative to the piston;

a lock configured to releasably lock the holder and the barrel to prevent relative motion between the holder and the barrel; and a transfer chamber for receiving the medicinal fluid from the vial, wherein the transfer chamber is in fluid communication with the needle;

wherein the needle retainer is configured so that the needle is automatically released for retraction at the end of an injection.

30. The device of claim 29 comprising a seal displaceable relative to the transfer chamber to expel the medicinal fluid from the transfer chamber.

31. The medical device of claim 29 wherein the holder Is at least partially disposed within the barrel.

32. The medical device of claim 29 wherein the holder is displaceable within the barrel.

33. The device of claim 29 wherein displacement of the holder relative to the barrel is operable to expel medicinal fluid from the transfer chamber through the needle.

34. The device of claim 29 wherein the holder is cooperable with the needle retainer to affect retraction of the needle.

35. The device of claim 29 wherein upon forward displacement of the vial holder, the vial holder contacts the needle retainer and displaces the needle retainer affecting retraction of the needle.

36. The medical device of claim 29 comprising a piston for expelling medicine out of the transfer chamber through the needle.

37. The medical device of claim 29 wherein the transfer chamber is displaceable relative to the needle.

38. The medical device of claim 29 comprising a valve adapted to control the flow of fluid between the transfer chamber and the vial.

39. The medical device of claim 38 wherein the valve is a sliding valve.

40. The medical device of claim 29 comprising a pierceable rear seal adapted to provide a fluid-tight seal between the vial and the transfer chamber.

41. The device of claim 40 comprising a pierceable forward seal providing a fluid-tight seal between the transfer chamber and the needle.

42. The device of claim 29 wherein the transfer chamber Is disposed within the barrel.

43. A medical device cooperable with a needle assembly having a retractable injection needle and a vial of medicinal fluid comprising:
- a housing cooperable with the needle assembly;
- a socket for receiving the vial, wherein the socket further comprises a piston external to the vial and within the housing to provide positive fluid pressure within the vial when the vial is positioned in the socket;
- an empty chamber in the housing for receiving the medicinal fluid from the vial;
- a transfer seal disposed between the socket and the chamber;
- a seal operable to retain fluid within the chamber when closed and to permit medicinal fluid to be expelled from the chamber through the needle when opened; and
- a valve to control the flow of fluid the between the vial and the chamber;
- wherein the housing has an activation surface cooperable with the needle assembly and configured to activate retraction of the needle after use.

44. The device of claim 43 wherein the seal comprises a pierceable seal sealing the chamber.

45. The device of claim 43 wherein the seal is positioned within the housing.

46. The device of claim 43 wherein the seal forms a forward end of the chamber.

47. The device of claim 43 wherein the seal is displaceable relative to the housing to expel the medicinal fluid from the chamber.

48. The device of claim 43 wherein the valve is a sliding valve.

49. The device of claim 43 comprising a stop for releasably retaining the housing from displacement relative to the needle assembly when the needle assembly is connected with the housing.

50. The device of claim 43 wherein the needle assembly comprises a needle retainer releasably retaining the needle, and wherein the housing is operable to contact the needle retainer to affect release of the needle for retraction.

51. The device of claim 43 wherein the piston is displaceable relative to the housing, and wherein displacing the piston forwardly is operable to pressurize the medicinal fluid in the vial.

* * * * *